United States Patent [19]

Fisanick

[11] Patent Number: 4,642,762
[45] Date of Patent: Feb. 10, 1987

[54] STORAGE AND RETRIEVAL OF GENERIC CHEMICAL STRUCTURE REPRESENTATIONS

[75] Inventor: William Fisanick, Columbus, Ohio

[73] Assignee: American Chemical Society, Washington, D.C.

[21] Appl. No.: 614,219

[22] Filed: May 25, 1984

[51] Int. Cl.$^4$ .............................................. G06F 15/40
[52] U.S. Cl. ................................................... 364/300
[58] Field of Search ... 364/200 MS File, 900 MS File

[56]  References Cited

U.S. PATENT DOCUMENTS 4,473,890  9/1984  Araki .................................... 364/900

*Primary Examiner*—Raulfe B. Zache
*Attorney, Agent, or Firm*—Philip J. Pollick

[57] ABSTRACT

An information retrieval system for storing and searching Markush formulations is described. All implicit specific structures (ISSRs) of the Markush formulation are stored as a specific multiple-connectivity node representation (SpMCN) by allowing the appropriate atoms to expand beyond their normal valance and accommodate all substituents of the Markush structure. The SpMCN is simplified by using a generic group hierarchy to reduce common structural features to an associated generic multi-connectivity node representation (GnMCN) that contains within it implicit generic structures (IGSRs) corresponding to each ISSR. Attributes such as ring size and hetero atom identification are also associated with each generic feature whenever possible. The SpMCN and GnMCN are further simplified by storing their associated structural characteristics as bit strings. To search the stored Markush formulations, a query structure is reduced to its generic structure, attributes, and associated structural characteristic bits strings. The bits strings are compared with the bit strings of the stored structures to eliminate stored structures without the requisite structural features. The generic structure and attributes of the query and remaining stored structures are then compared on a group by group basis and additional structures are thereby eliminated from the search. Finally the specific structure of the query is compared with the specific structures of the remaining stored structures to determine more precisely if there is a match. Reference data, such as patent numbers, are then retrieved for the matched structures.

31 Claims, 22 Drawing Figures

FILE
GnMCN | IGSR
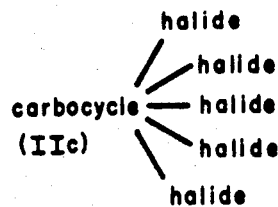 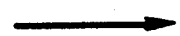 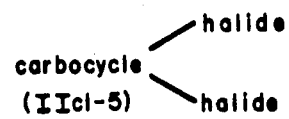
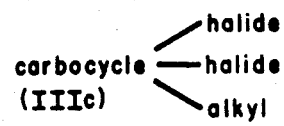  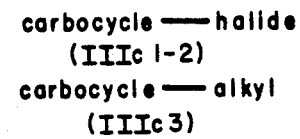
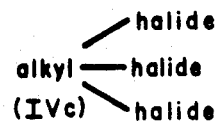  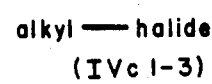
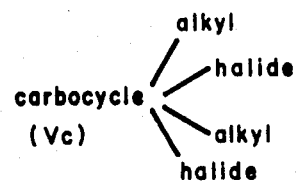  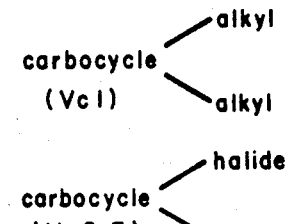
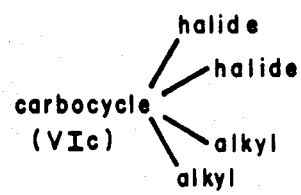 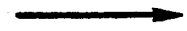 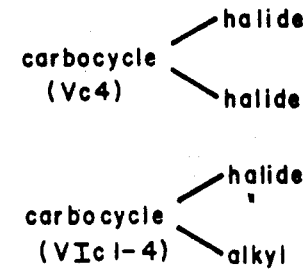
FIG. 3

QUERY

GnMCN                                      IGSR carbocycle — halide              carbocycle — halide
(VIIc)    — alkyl      ⟶         (VIIc1)   — halide
          — halide carbocycle — alkyl
                                 (VIIc2)    — halide

FIG. 3'

Explicit
Query
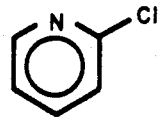
(VIII)
File
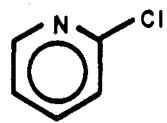
(X)
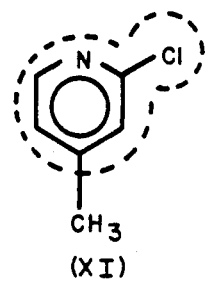
(XI)
Markush
SpMCN
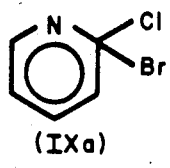
(IXa)
ISSR
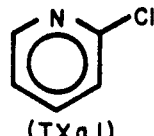
(IXa1)
(IXa2)
SpMCN
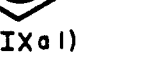
(XIIa)
ISSR
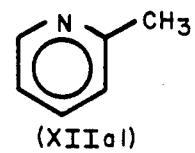
(XIIa1)
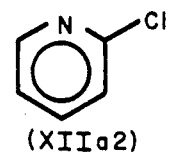
(XIIa2)
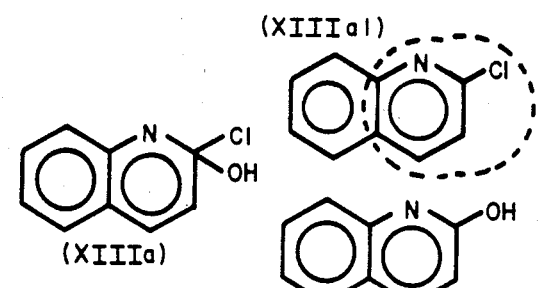
(XIIIa)
(XIIIa1)
(XIIIa2)
FIG. 5

MARKUSH
(XVIIIa)
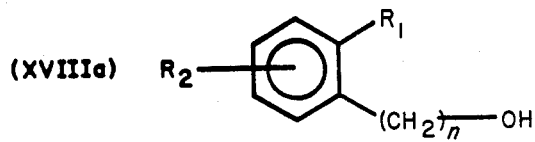
$R_1$ = OMe, Alkyl Group, Electron-withdrawing Group
$R_2$ = Heterocyclyl, Cl
$n$ = 1-3
If $R_1$ = OMe, then $R_2$ = Cl
↓
SpMCN
(XVIIIb)
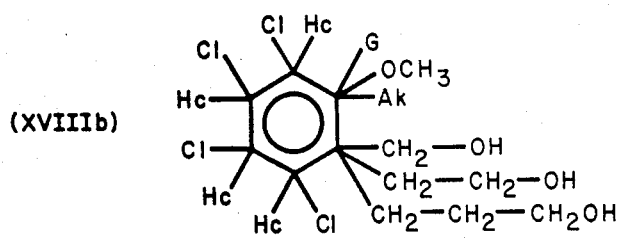
↓
GnMCN
(XVIIIc)
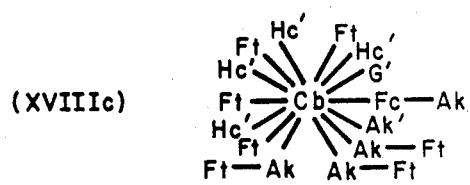
FIG. 8

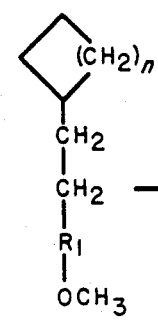
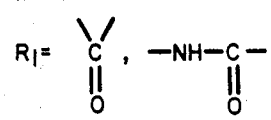
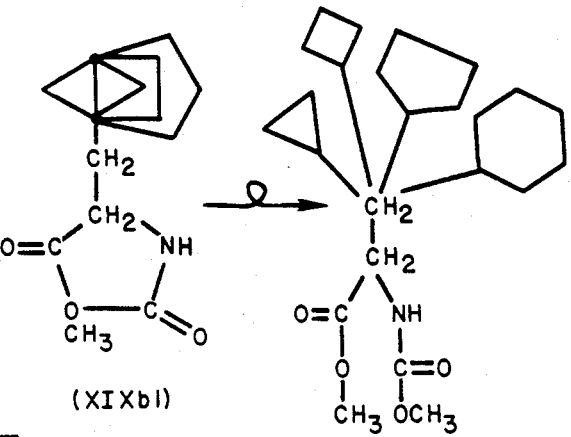
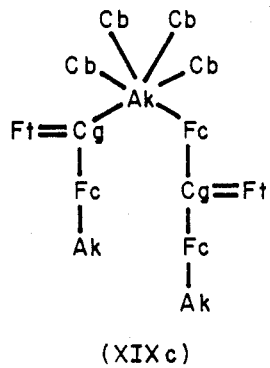
FIG. 9

| Attributes: | (a) | (b) | (c) | (d) |
|---|---|---|---|---|
| 1. Heteroatoms | — | N(≥1) | — | N(1) |
| 2. Ring Size | — | — | 6 | 6 |
| 3. Bonds | — | — | — | 6 all normalized |

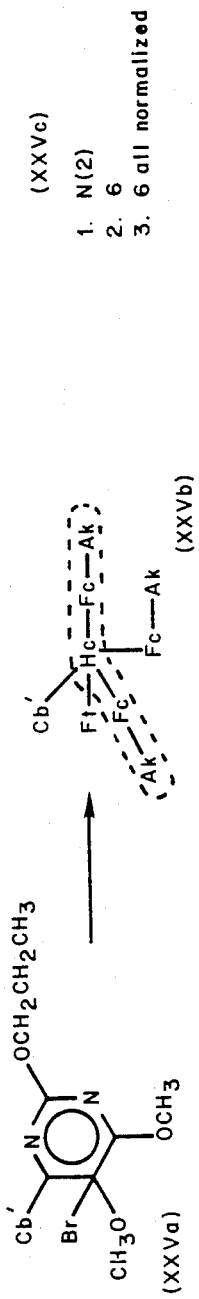
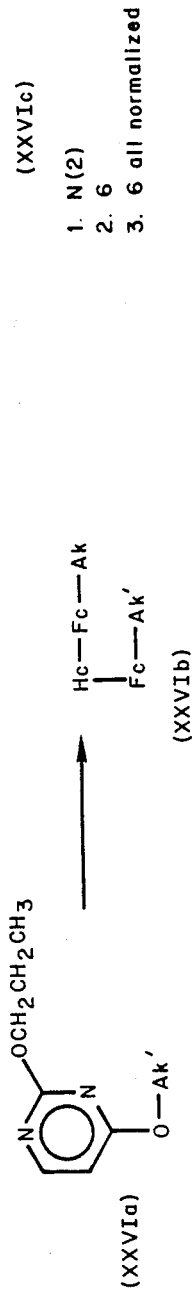
FIG. 13'

Markush
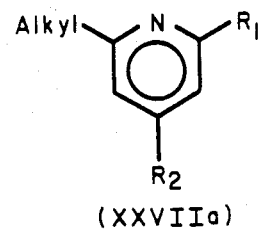
(XXVIIa)
$R_1$ = Br, Cl, OCH$_3$
$R_2$ = N(CH$_3$)$_2$, NHCH$_2$CH$_2$–R$_3$
$R_3$ = OCH$_3$, SCH$_3$
↓
SpMCN
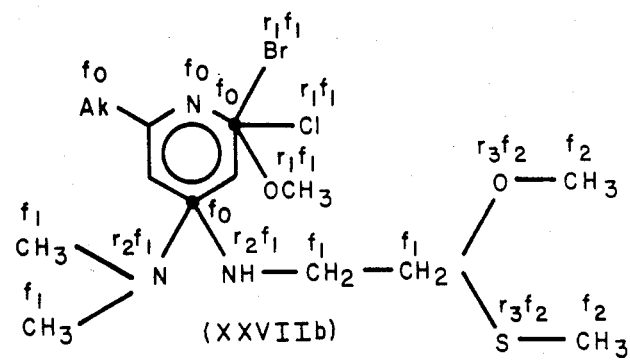
(XXVIIb)
↓
GnMCN
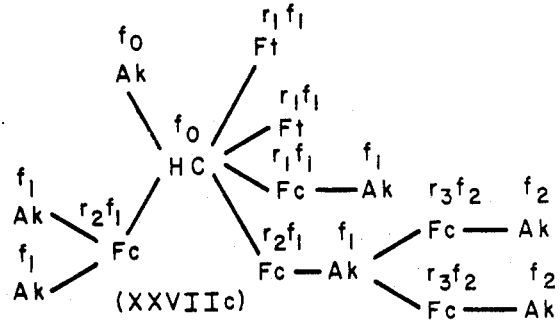
(XXVIIc)
FIG. 14

| Query | | File | |
|---|---|---|---|
| SpMCN | GnMCN | GnMCN | SpMCN |
 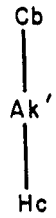 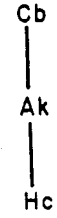 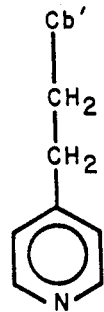
(XXVIIIa)   (XXVIIIb)   (XXIXb)   (XXIXa)
FIG·15

FILE
SpMCN
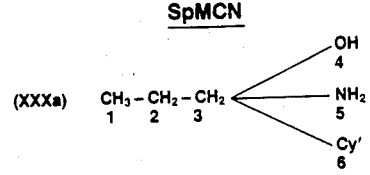
(XXXa)
Specific-Atom Screens
| AA | No. | AA | No. | AS | No. |
|---|---|---|---|---|---|
| C-C<br>1 2<br>2 3 | 1 | C-C-N<br>3 2 5 | 5 | C-C-C-O<br>1 2 3 4 | 17 |
|  |  | O-C<br>4 3 | 6 | C-C-C-N<br>1 2 3 5 | 19 |
| C-C-O<br>3 2 4 | 4 | N-C<br>5 2 | 7 |  |  |
Specific Atom Bit String
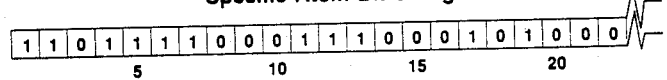
GnMCN
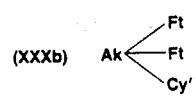
(XXXb)
Generic-Group Screens
| AA | No. |
|---|---|
| Ak-Ft | 31 |
| Ak-Cy | 33 |
| Ak-Cb | 34 |
| Ak-Hc | 35 |
Generic-Group Bit String
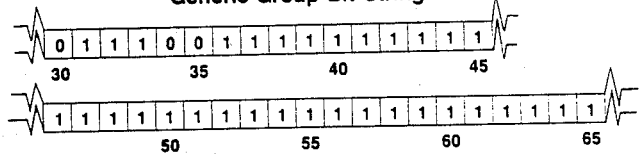
Diagnostic Screens
| Screen | No. |
|---|---|
| Cy' | 72 |
| Cb' | 73 |
| Hc' | 74 |
Diagnostic Bit String
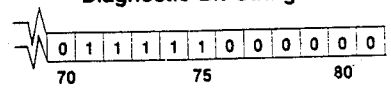
FIG. 16

QUERIES
| SpMCN | | | | GnMCN | |
|---|---|---|---|---|---|
| Screen | No. | | | Screen | No. |
| C | 11 | | | | |
| C-C | 1 | | | | |
| C-C-C | 2 | | Ak | AK | 58 |
| Cl | 14 | (XXXIa) | (XXXIb) | Ft | 55 |
| O | 13 | | | | |
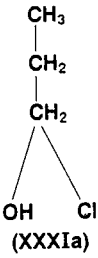
| | | | | | |
|---|---|---|---|---|---|
| C | 11 | | | | |
| C-C | 1 | | Ak | Ak | 58 |
| C-C-C | 2 | | | | |
| | | (XXXIIa) | (XXXIIb) | Hc | 54 |
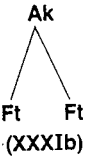
| | | | | | |
|---|---|---|---|---|---|
| C | 11 | | | | |
| C-C | 1 | | Ak | Ak | 58 |
| C-C-C | 2 | | | | |
| | | (XXXIIIa) | (XXXIIIb) | Cb | 53 |
| C*C | 15 | | | | |
| C*C*C | 8 | | | | |
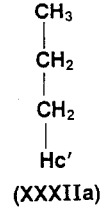
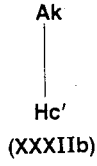
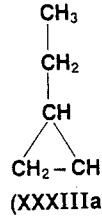
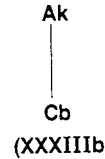
FIG. 17

STORAGE AND RETRIEVAL OF GENERIC CHEMICAL STRUCTURE REPRESENTATIONS

FIELD

This invention relates to a method for storing and retrieving generic chemical structure representations (Markush formulations) and information associated with them. It is directed especially to development of specific(real)-atom and generic-group representations of the Markush formulation that are used in atom-by-atom and group-by-group comparison of query and file representations and the use of screening techniques to eliminate a high percentage of irrelevant file representations prior to group-by-group and atom-by-atom comparison of generic-group and specific-atom representations.

BACKGROUND

The ability to effectively retrieve information on generic chemical structures, i.e., so-called Markush structures, has been a problem of varying magnitude and complexity since the inception of the use of the Markush claim by the Patent Office in the 1920's. Many manual and mechanized information retrieval systems have been developed to meet the challenge of this problem but the known techniques for such retrieval are imprecise and often place a premium on the knowledge, intuition, and cognitive skills of the searcher.

The basic system for dealing with Markush structures is a manual system in which individual documents containing the Markush structure are classified according to a highly refined classification system and physically grouped according to the classification scheme into a search file. In making a search, the searcher proceeds by classifying the document (query) in hand and then goes to the appropriately classified physical group of documents in the search file and manually searches those documents for relevant retrievals. Such a system places a high premium on the correct initial classification of search file documents, correct classification of the query, physical search-file integrity, and highly-developed cognitive skills of the searcher. Moreover, because the Markush may represent thousands or even millions of compounds, it often is impossible to promulgate copies of the document into all of the search file classifications represented by the Markush formulation. Weaknesses in any of the aforementioned areas is likely to produce unsatisfactory search results. (U.S. Department of Commerce, "Development and Use of Patent Classification Systems", U.S. Government Printing Office, Washington, D.C., 1966.)

Another technique used in both manual and mechanized systems for the handling of Markush structures involves the use of a system of fragmentation codes that are in effect generic or real-atom "group" representations of portions of a particular Markush formulation. For example, that portion of the formulation containing chains of carbon atoms might be generically encoded as alkyl, or OH group as an alcohol or hydroxide, and F, Cl, Br, and I as a halide. Real-atom groups, such as methyl for $CH_3$13, ethyl for $CH_3CH_2$—, and phenyl for $C_6H_5$—, are also typically used. (Balent, M. Z.; Emberger, J. M. "A Unique Chemical Fragmentation System for Indexing Patent Literature" *J. Chem. Inf. Comput. Sci.* 1975, 15, 100–104. Kaback, S. M. "Chemical Structure Searching in Derwent's World Patents Index" *J. Chem. Inf. Comput. Sci.* 1980, 20, 1–6. Rossler, S.; Kolb, A. "The GREMAS System, an Integral Part of the IDC System for Chemical Documentation" *J. Chem. Doc.* 1970, 10, 128–134. Rowlett, R. J. "Gleaning Patents with Chemical Abstracts" *Chemtec.* 1979, June, 348–349. Silk, J. A. "Present and Future Prospects for Structural Searching of the Journal and Patent Literature." *J. Chem. Inf. Comput. Sci.* 1979, 19, 195–198.) However, the inter-relationships among these groups in a Markush formulation are typically not encoded. As a result, such systems tend to have good recall, i.e., most of the relevant search file answers are retrieved but, because the inter-relationship among the groups can not be specified and the reliance on generic terminology, such systems have a pronounced tendency to lack precision, i.e., many of the answers retrieved are irrelevant to the query. Precision has been improved by incorporation of a higher degree of specificity into the fragmentation codes, but only at a price paid in terms of higher complexity and difficulty in file encoding and search profile formulation and a resulting higher potential for error.

Mechanized specific atom-by-atom structure matching of query and file structural representations is a well-known commercial technique that has been available since the 1960s and has demonstrated high recall and precision as a search and retrieval technique. (Wigington, R. L. "Machine Methods for Accessing Chemical Abstracts Service Information in *Proceedings of the IBM Symposium on Computers and Chemistry*"; IBM Data Processing Division: White Plains, NY, 1969. Eakin, D. R. "The ICI CROSSBOW System," in Ash, J. E.; Hyde, E., Eds. *Chemical Information Systems*, Chichester, Horwood, 1975. Dubois, J. E. "DARC System in Chemistry", in *Computer Representation and Manipulation of Chemical Information*, Wipke, W. T.; Heller, S.; Feldman, R.; Hyde, E., Eds., Wiley, New York, 1974. Schenk, H. R.; Wegmuller, F. "Substructure Search by Means of the Chemical Abstracts Service Chemical Registry II System" *J. Chem. Inf. Comput. Sci.* 1976, 16, 153–161. Feldman, R. J. "Interactive Graphic Chemical Substructure Searching" in *Computer Representation and Manipulation of Chemical Information*, Wipke, W. T.; Heller, S.; Feldman, R.; Hyde, E., Eds., Wiley, New York, 1974.) Because atom-by-atom structure matching is a relatively slow process, screening techniques have been developed to eliminate a high percentage of irrelevant file representations. Typically screening involves capturing key features of the file representations such as atom environment and atom sequences and then matching similar key features of the query representation to give a set of answers that are then used in atom-by-atom structure matching. (Dittmar, P. G.; Farmer, N. A.; Fisanick, W.; Haines, R. C.; Mockus, J. "The CAS ONLINE Search System. 1. General System Design and Selection, Generation, and Use of Search Screens" *J. Chem. Inf. Comput. Sci.* 1983, 23, 93–102. Attias, R. "DARC Substructure Search System: A New Approach to Chemical Information" *J. Chem. Inf. Comput. Sci.* 1983, 23, 102–108.) Unfortunately, structure matching techniques tend to be limited to files containing representations of unique individual compounds and queries have been limited to specific structural representations that must exactly match the structural representation of the file compound (full-structure search) or be embedded within it (substructure search). Structure matching techniques have been applied to Markush formulations which represent a relatively small number of specific compounds using queries that contain only real atoms. (Meyer, E. "Topological Search for Classes of Compounds in Large Files—even of Markush Formulas—at Reasonable Machine Cost" in *Computer Representation and Manipulation of Chemical Information*, Wipke, W. T.; Heller, S.; Feldman, R.; Hyde, E., Eds., Wiley, New York, 1974.) However, in attempting to apply structure matching techniques to query and file structures represented by Markush formulations of the type often found in broad patent claims, one is immediately faced with the problem that a single Markush formulation may literally represent millions of specific compounds. When one considers that the file size of the current large commercial structural matching systems is a little less than seven million specific compounds, an appreciation is gained for the difficulty in using structure matching techniques to search effectively Markush structures. Although proposals have been made to apply structure matching techniques to broad Markush formulations, no viable system for searching such Markush formulations that gives a high degree of recall and precision has yet been achieved. (Lynch, M. F.; Bernard, J. M.; Welford, S. M. "Computer Storage and Retrieval of Generic Chemical Structures in Patents. 1. Introduction and General Strategy" *J. Chem. Inf. Comput. Sci.* 1981, 21, 148–150. Barnard, J. M.; Lynch, M. F.; Welford, S. M. "Computer Storage and Retrieval of Generic Chemical Structures in Patents. 2. GENSAL, a Formal Language for the Description of Generic Chemical Structures" *J. Chem. Inf. Comput. Sci.* 1981, 21, 151–161. Welford, S. M.; Lynch, M. F.; Barnard, J. M. "Computer Storage and Retrieval of Generic Chemical Structures in Patents. 3. Chemical Grammars and their Role in the Manipulation of Chemical Structures" *J. Chem. Inf. Comput. Sci.* 1981, 21, 161–168. Barnard, J. M.; Lynch, M. F.; Welford, S. M. "Computer Storage and Retrieval of Generic Chemical Structures in Patents. 4. An Extended Connection Table Representation (ECTR) for Generic Structures." *J. Chem. Inf. Comput. Sci.* 1982, 22, 160–164. Nakayama, T.; Fujiwara, Y. "Computer Representation of Generic Chemical Structures by an Extended Block-Cutpoint Tree" *J. Chem. Inf. Comput. Sc* 1983, 23, 80–87. Kudo, Y.; Chihara H. "Chemical Substance Retrieval System for Searching Generic Representations. 1. A Prototype System for the Gazetted List of Existing Chemical Substances of Japan" J. Chem. Inf. Comput. Sci. 1983, 23, 109–117.)

SUMMARY

A typical Markush storage and retrieval process according to the resent invention comprises the steps of forming a file of structural representations of Markush formulations in which each Markush formulation is represented by a single specific atom multiple connectivity node (SpMCN) representation in which the formal valance requirements of requisite atoms are relaxed to allow for the attachment of all atoms and groups of atoms depicted in the Markush formulation and, as a result, gives a representation containing all implicit specific atom structures found in the Markush formulation. The SpMCN is then converted to an associated generic group multiple connectivity node (GnMCN) representation through the use of a generic-group hierarchy. A query Markush formulation is similarly converted to SpMCN and GnMCN representations. The query GnMCN representation then is compared on a group-by-group basis with each file GnMCN in such fashion so that a match is found when at least one implicit generic structure representation (IGSR) of the query GnMCN is identical with (overlaps) or is contained in (embedded in) at least one IGSR of the file GnMCN. The query SpMCN representation then is compared on an atom-by-atom basis with the file SpMCN representations associated with the file GnMCN representations (answers) obtained in the previous query GnMCN/file GnMCN matching step in such fashion so that a match is found when at least one implicit specific atom structure representation (ISSR) of the query SpMCN structure is identical with (overlaps) or is contained in (embedded in) at least one ISSR of the file SpMCN. An indexing system is used to identify IGSRs and ISSRs for the matching process and to manipulate large or complex GnMCN and SpMCN representations.

As a further refinement, generic features of the original Markush formulation are captured by using the generic-group hierarchy as a means of representing generic features of the Markush formulation in both the SpMCN and GnMCN. To insure high recall, a roll-back feature is used to allow for the exchange of generic-group and specific-atom representations in SpMCN matching so that all real atom file or query structural features implied in the generic structural features of the file or query SpMCN are matched. In addition, specific features of the SpMCN and specifically identified parts of generic features of the original Markush formulation, such as specific atoms, type of bonding, ring size, etc. are associated with each generic group of the file GnMCN as group attributes and are matched against group attributes of the generic groups of the query GnMCN prior to SpMCN matching.

As a further refinement, screening techniques are applied to both SpMCN and GnMCN representations in order to eliminate a large number of irrelevant file representations prior to the more exacting group-by-group and atom-by-atom comparisons. In order to achieve a high level of recall, a Boolean strategy is used in the query screen logic expression whereby special, "diagnostic" generic-group screens are used as alternatives for sets of specific-atom screens in order to retrieve file answers in situations where real-atom structures of the SpMCN query structure are implied in the generic portions of the file SpMCNs that originate from generic features of the original Markush formulation and for which there are no real-atom counterparts.

DRAWINGS

FIG. 1 illustrates a Markush structure and its associated Multiple Connectivity Node (SpMCN) and Generic Multiple Connectivity Node (GnMCN) structures.

FIGS. 2 and 2' illustrate file and query SpMCN and GnMCN structures.

FIGS. 3 and 3' illustrate query and file GnMCN matching using implicit generic-group structural representations (IGSRs).

FIG. 5 illustrates query ISSR overlap with and embedment in file ISSRs.

FIG. 8 illustrates the handling of complex features of a Markush formulation in associated SpMCN and GnMCN structures.

FIG. 9 illustrates simplification of a complex ring and pseudo-ring features of the SpMCN and GnMCN representations by shifting of the point of variability.

Figure 11:
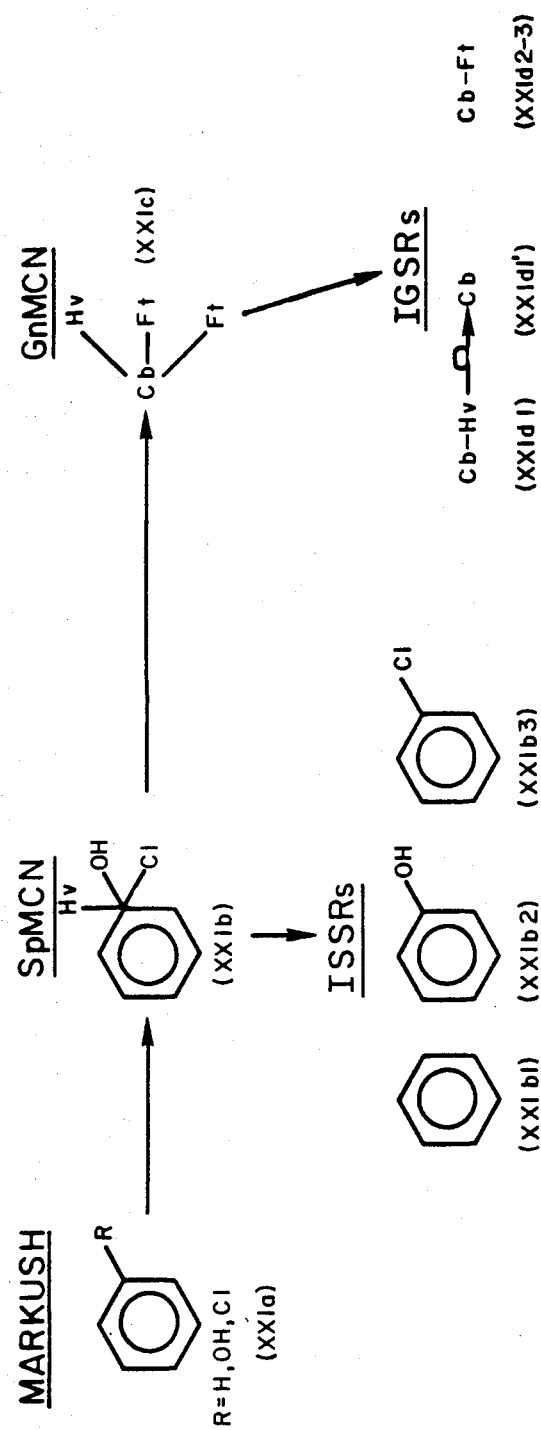
Figure 11:
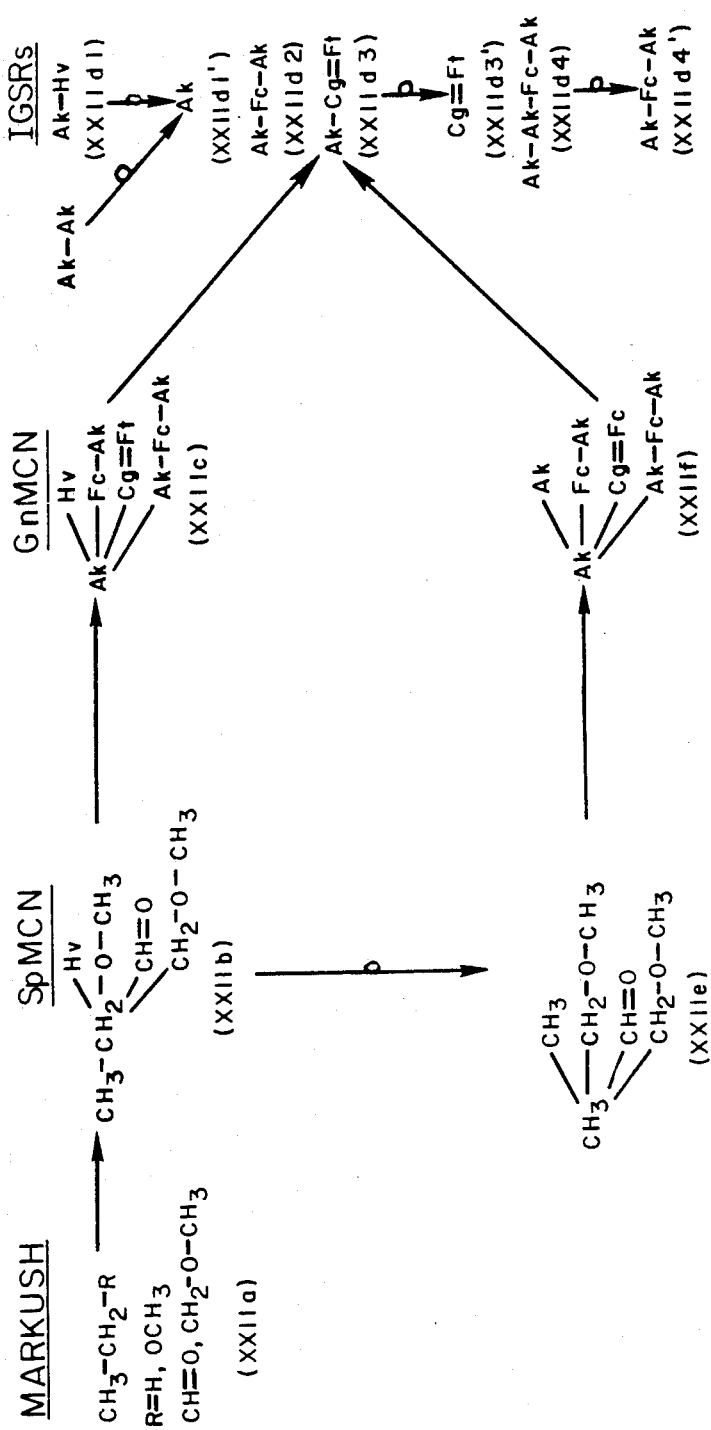

FIGS. 11 and 11' illustrate the handling of "variable" hydrogen and simplification of forbidden generic group combinations in SpMCN and GnMCN representations.

Figure 12:
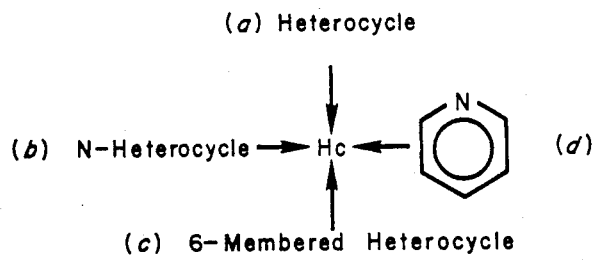

FIG. 12 illustrates generic group attributes of the GnMCN structure.

Figure 13:
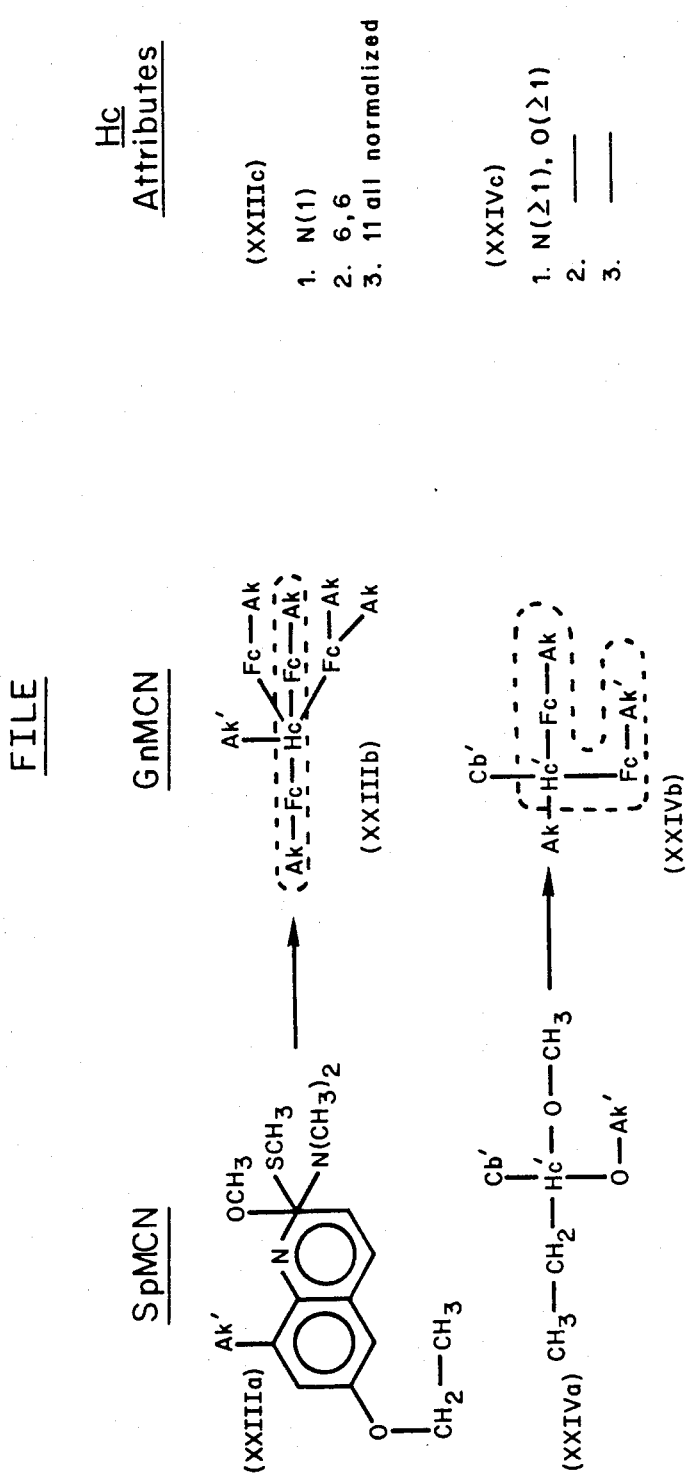

FIGS. 13 and 13' illustrate matching of query and file generic-group attributes.

FIG. 14 illustrates node flagging of SpMCN and GnMCN structures.

FIG. 15 illustrates roll-back of segments of the ISSR to the generic group in matching ISSRs of query and file SpMCN representations.

FIG. 16 illustrates SpMCN and GnMCN representation using screens and bit strings.

FIG. 17 illustrates SpMCN and GnMCN query formulation using logic expressions for individual ISSR and IGSRs.

Figure 18:
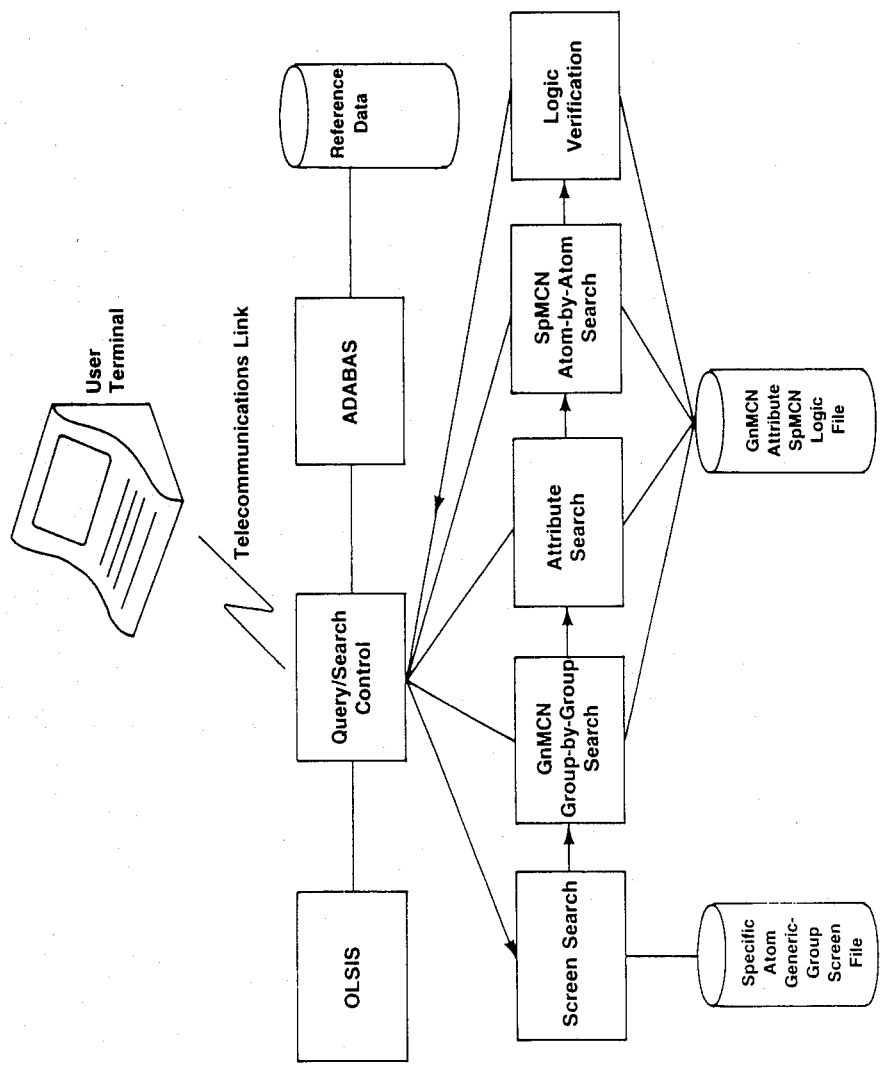

FIG. 18 illustrates Markush formulation search and retrieval using a general computer system.

DETAILED DESCRIPTION

Figure 1:
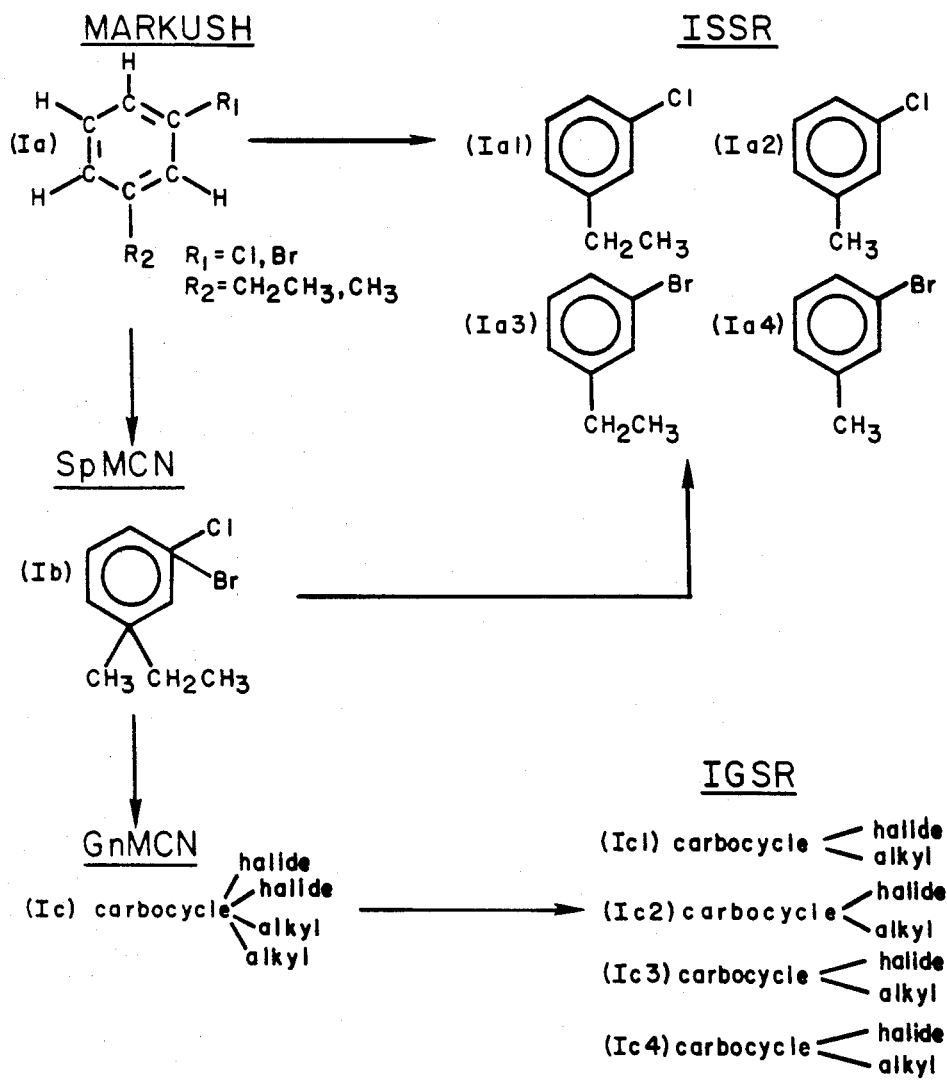

A simple Markush formulation is set forth in structure Ia of FIG. 1. This formulation consists of a fixed structure portion to which is attached the variable groups $R_1$ and $R_2$. As indicated in the text portion of the formulation, $R_1$ may be chlorine (Cl) or bromine (Br) and $R_2$ may be ethyl ($CH_3CH_2$) or methyl ($CH_3$). Implicit in the Markush formulation is the representation of four distinct individual compound representations, Ia1–Ia4, that are, in effect, all of the possible individual structures resulting from the combinations of fragments in the variable groups denoted by $R_1$ and $R_2$.

In representation Ia, it is noted that carbon (C) typically has a connectivity (valance) of four, i.e., is capable of attaching or connecting itself to four other entities or to fewer than four other entities via a multiple bond to one or more of the entities. Specifically in the ring system of representation Ia, each carbon is bound to a second carbon by a multiple (double) bond, to a third carbon atom by a single bond, and to a hydrogen atom (H) or to a variable group node ($R_1,R_2$) by a single bond to give the usual carbon valance of four. As is shown in structures Ia1–Ia4, it is common practice in the chemical arts often to omit the hydrogen atoms and to designate the alternate single and double bonds between carbon atoms in the ring as a circle, the later convention is felt to represent more realisticly a delocalized bonding situation in which there are more like one and a half bonds between all carbon atoms. Except where noted, these common conventions will be followed throughout the remainder of the specification and drawings.

Structure Ib of FIG. 1 is a multiple connectivity node (MCN) structure. In it, all of the fragments belonging to the variable groups described in the text part of the Markush formulation have been attached to their respective nodes or points of variability (as shown in the structure part of the Markush formulation Ia) giving rise to nodes of abnormally high connectivity and hence the multiple connectivity node (MCN) designation. Since Ib represents all of the specific atoms identified in the Markush formulation, it is designated as a specific-atom multiple connectivity node (SpMCN) representation. It should be noted that the four distinct individual compound representations, Ia1–Ia4, are also implicit in the SpMCN. These individual implicit representations are referred to as implicit specific-atom structural representations (ISSRs).

By using common generic technology, it is possible to simplify further the specific multiple connectivity node structure (SpMCN). For example, carbon ring structures containing only carbon atoms in the ring are often given the generic description of carbocycles; linear chains of carbon atoms are generically termed alkyls; and chlorine and bromine are often called halides. Using this basic generic terminology, it is possible to transform the SpMCN representation shown in Ib to the generic multiple connectivity node representation (GnMCN) shown in Ic. In transforming the SpMCN to a GnMCN, the bonding level between the generic groups is preserved. In this particular example, only a single bond exists between the carbocycle and the variable groups. If, however, a multiple bond exists between the generic representations, such bonding is indicated in the GnMCN. Implicit within the GnMCN representation are four implicit generic group structure representations (IGSRs), Ic1–Ic4, corresponding to the four distinct compound representations, ISSRs, implicit in the original Markush and the SpMCN. It is critical to note that IGSRs and ISSRs are used for illustrative purposes only. This invention does not anticipate the storage of all ISSRs and IGSRs associated with the respective SpMCN and GnMCN. Rather the invention is directed at the indivdiual ISSRs and IGSRs as they are implicitly contained within the SpMCN and GnMCN. The actual representation and processing uses only the explicit SpMCN and GnMCN representations. The ISSRs and IGSRs are used only as they are implicitly found within the SpMCN and GnMCN representations.

Figure 2:
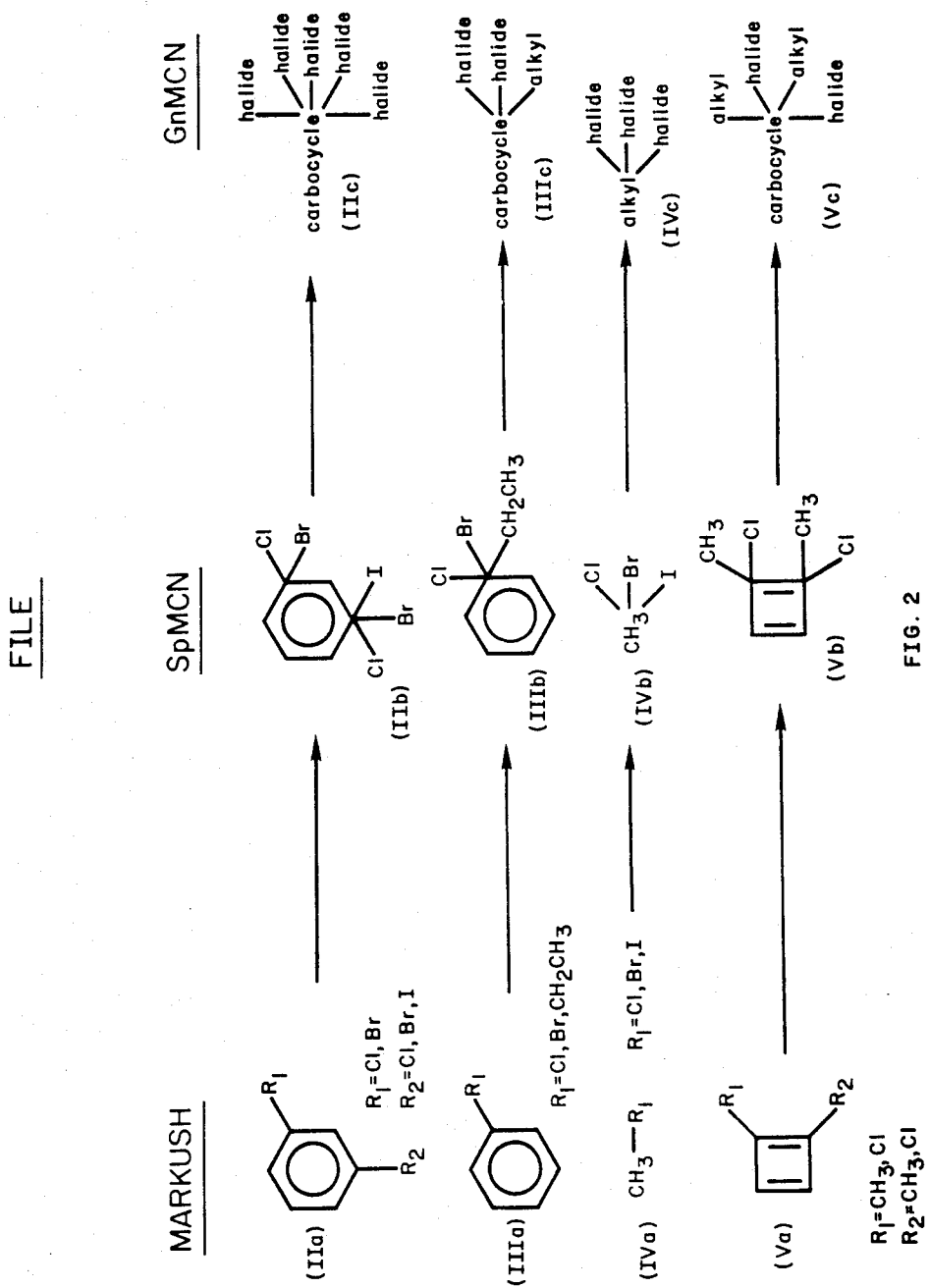
Figure 2:
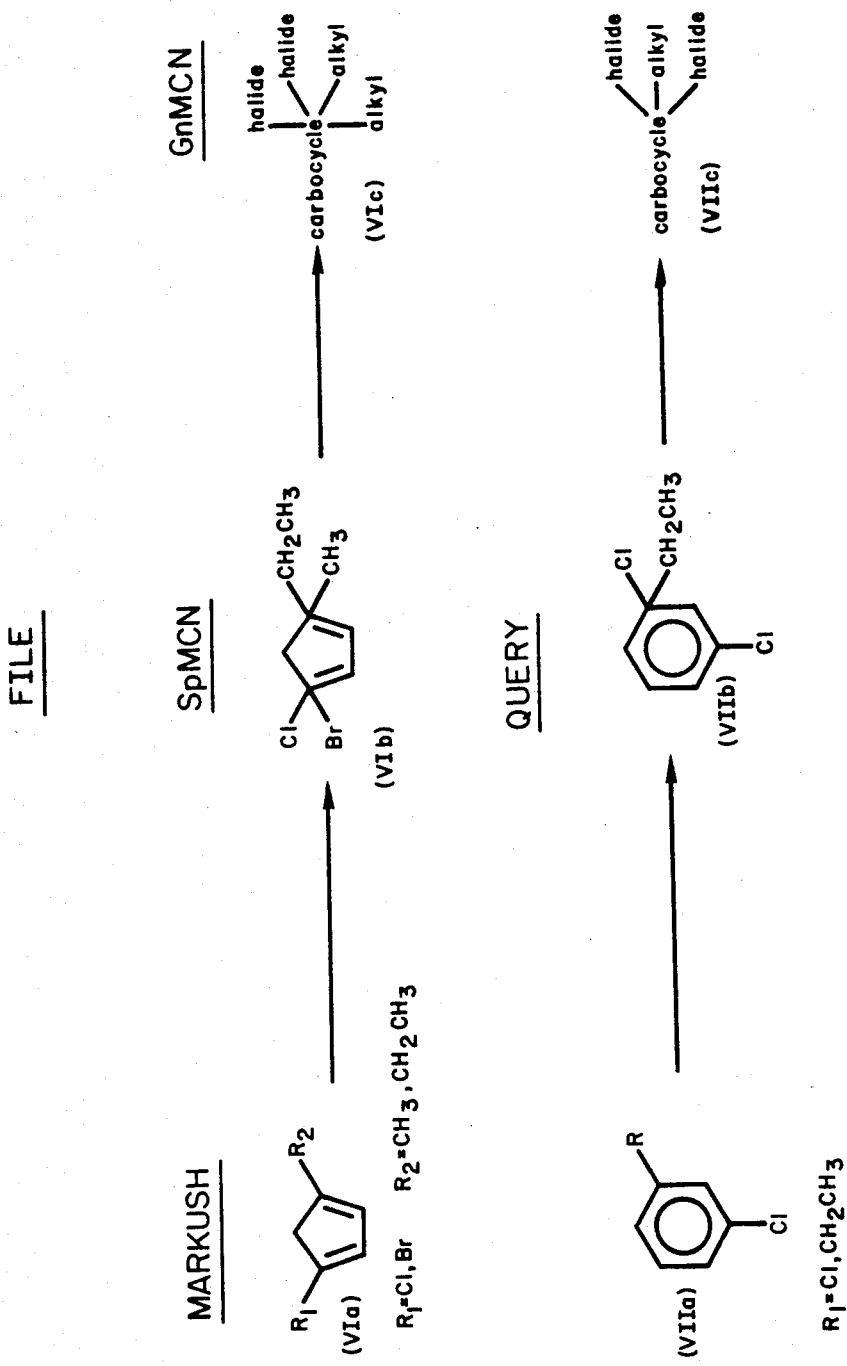
Figure 4:
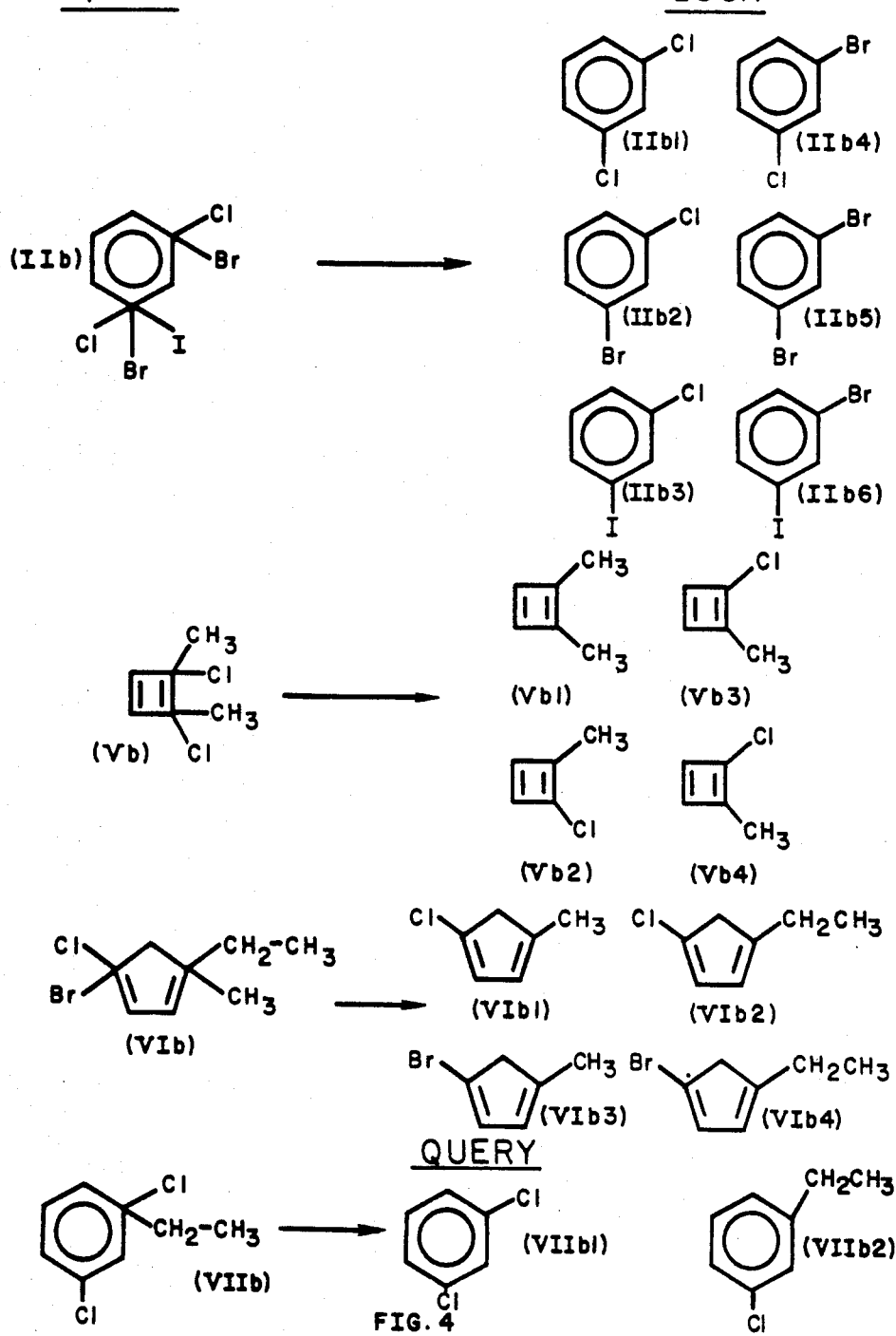
FIG. 4 illustrates query and file SpMCN matching using implicit specific-atom structural representations (ISSRs).

FIGS. 2, 2', 3, 3' and 4 illustrate the use of the GnMCN and SpMCN representations in file searching and retrieval. In FIGS. 2 and 2', representations IIa–VIa are illustrative file Markush formulations as they might appear in patent documents, IIb–VIb are SpMCN representations of the corresponding Markush formulation, and IIc–VIc are GnMCN representations of the corresponding SpMCN representations. The query Markush formulation VIIa is also shown as a SpMCN representation (VIIb) and a GnMCN representation (VIIc). As shown in FIGS. 3 and 3', a file search is initiated by comparing each query IGSR (VIIc1 and VIIc2) with each file IGSR (11c1–IIc5, IIIc1–IIIc3, IVc1–IVc3, Vc1–Vc4, and VIc1–VIc4; identical implicit structures are shown only once). As seen, query IGSR VIIc1 matches with file IGSRs IIc1–IIc5 and Vc4; VIIc2 matches with Vc2–Vc3 and VIc1–VIc4. At this point, representations III and IV have been eliminated from the search and, as shown in FIG. 4, matching now proceeds between the query ISSRs VIIb-1–VIIb2 and the file ISSRs IIb1–IIb6, Vb1–Vb4, and VIb1–VIb4; query ISSR VIIb1 matches only with file ISSR IIb1 and query ISSR VIIb2 matches nothing, specifically illustrating that only one ISSR need match one file ISSR to give an answer. To complete the search, relevant information associated with the Markush formulation IIa such as, but not limited to, an abstract, patent number, or patent document is retrieved for the searcher.

FIG. 5 illustrates the two types of matching criteria that a searcher may use in carrying out a search. Representation VIII is a single compound representation in which the ISSR is identical with the actual structure. This structure matches exactly with the file representation X which is also a single compound representation. The exact matching of all characteristics of the query representation with those of the file representation is termed "overlap" or full-structure search. Exact matching may be relaxed such that the query representation need only be contained within the file representation. Thus, although query representation VIII does not exactly match or "overlap" the single file representation XI, it is contained within representation XI. Such containment of the query representation within the file representation is termed "embedment" or substructure search. Systems for both full-structure and substructure search are commercially available, e.g., CAS ONLINE: The Registry File, Chemical Abstracts Service, Columbus, Ohio.

Atom-by-atom searching involves the comparison of a query structure with a file structure using a path-tracing technique. Typically the path-tracing technique involves selecting a starting atom (node) of the query structure (usually a noncarbon atom) and comparing it with the first atom of the file structure. If the atoms do not match, the file structure is advanced to the next atom (node) until a match with the starting query node is obtained. If a match is obtained, the query proceeds to the next connected atom which is compared with the next connected atom of the file structure. If these next atoms do not match, the file structure is backtracked to the original matching atom and another connected atom is selected for match. This advancing/comparing/backtracking routine is continued until all atoms match or all atom sequences of the query are exhausted. Overlap requires that all atoms of the query match with all atoms of the file structure while embedment requires that all of the atoms of the query be contained within the file structure. A description of atom-by-atom matching is given in Lynch, M. F.; Harrison, J. M.; Town, W. G.; Ash, J. E. *Computer Handling of Chemical Information*, MacDonald, London and American Elsevier Inc., New York, 1971 at pp. 73–74, all of which is herein incorporated by reference.

It is an object of this invention to extend both the overlap and embedment matching concepts to Markush searching. Thus if the query SpMCN IXa search is limited to overlap only, the query ISSR IXa1 will match only with file ISSR XIIa2. If the matching criterion is relaxed to embedment, ISSR XIIIa1 is also a valid match. It is not necessary to limit the searching of a Markush query to a Markush file, e.g., the ISSRs of the SpMCN representation also can be compared with both specific compound representations such as X and XI and the ISSRs of the SpMCN representations XIIa and XIIIa. At the overlap level of search, query IXa retrieves file representations X and XIIa; at the embedment level of search, file representations X, XI, XIIa, and XIIIa are retrieved. Single specific compound queries also can be searched against the Markush file, e.g., VIII matches with XIIa1 (overlap) and with XIIIa1 (embedment). Although not illustrated, embedment and overlap criteria are also used at the generic level of searching. Thus an implicit generic query representation, alkyl-halide, overlaps an implicit generic file representation, alkyl-halide, and is embedded in an implicit generic file representation, carbocycle-alkyl-halide. Finally it is noted that the overlap criterion can be applied to the entire SpMCN representation itself. Such a match condition requires all structural elements of the file SpMCN be identical to all structural elements of the query SpMCN, i.e., all ISSRs or the file and query SpMCNs must be identical. Requiring the entire SpMCN representation IXa to match at the overlap level permits only the retrieval of file SpMCNs that are identical to it, i.e., contain both IXa1 and IXa2 but only those two implicit representations. For an entire SpMCN representation to match at the embedment level, the file SpMCN representation must contain all ISSRs of the query representation.

Figure 6:
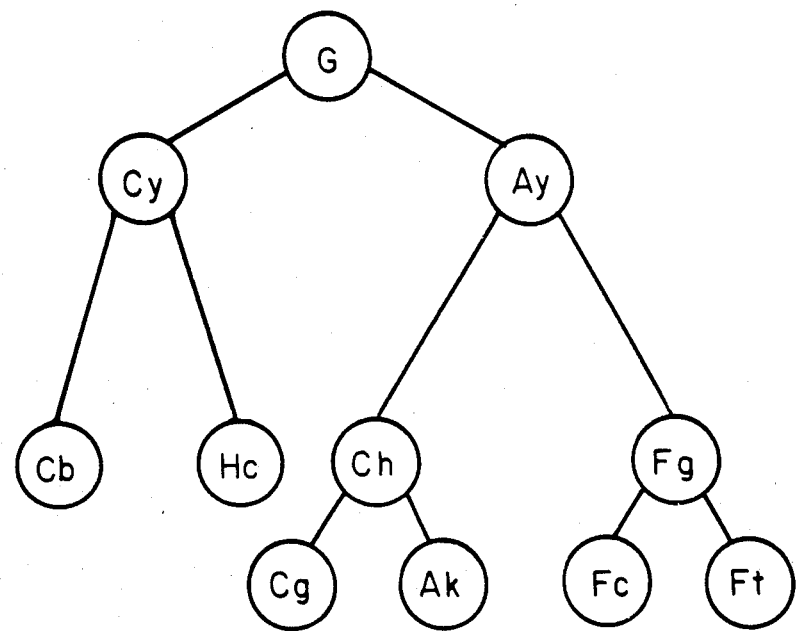
FIG. 6 is a hierarchical classification scheme for converting SpMCN representations to GnMCN representations and for encoding generic features found in the original Markush formulation.

In order to convert SpMCN representations to GnMCN representations, it is highly desirable to have a classification scheme that uses a small number of controlled-vocabulary hierarchical terms that permit classification of all groups of atoms likely to be encountered in a specific substance or a Markush formulation. FIG. 6 illustrates such a classification scheme. The overall structure of the classification scheme consists of breaking each less-specific group into two mutually exclusive, more specific groups. The general group "G" is used to handle groups of atoms that can not be easily associated with a more specific group classification, e.g., an electron-withdrawing group, a group containing nitrogen, etc. The G group is classified further into two mutually exclusive groups: any cyclic group (Cy) or any acyclic group (Ay). The cyclic group (Cy) is broken down into any carbocycle group (Cb) or any heterocycle group (Hc). The carbocycle group (Cb) characterizes any ring system containing only carbon atoms and any attached hydrogen atoms. The Cb group may be attached to any other group, including itself, or it may stand alone. The heterocycle group (Hc) characterizes any ring system containing one or more hetero (noncarbon) atoms and any attached hydrogen atoms. Similar to Cb, Hc may be attached to any group, including Hc, or it may stand alone. A fused ring system, i.e., two or more rings joined at two or more atoms on each ring with each other, is considered a single group while two rings joined to each other by an acyclic bond is considered as two groups. Thus a naphthalene ring system is designated as Cb while a biphenyl system would be characterized as Cb—Cb. A quinoline ring system, which consists of a carbocycle fused to a heterocycle, is considered as a single heterocycle group, Hc.

Moving to the acyclic side of the hierarchy, the acyclic group (Ay) is broken down into any acyclic carbon (chain) group (Ch) or any acyclic noncarbon (functional) group (Fg). The acyclic noncarbon group (Fg) is further broken down into any acyclic noncarbon connecting group (Fc) or any acyclic noncarbon terminal group (Ft). The terminal group (Ft) is characterized as a single atom that is neither carbon or hydrogen but may be attached to one or more hydrogens. The Ft group may stand alone (unattached to any other group), e.g. $NH_3$, $H_2O$, Cu, or it may be attached to one and only one other group where the other group may be any other group including Ft except that the Ft group cannot be bound to an alkyl group (Ak) by a multiple bond since, by definition, an alkyl group bound to a Ft group by a multiple bond is a Cg group. Thus $C_6H_5$—$NH_2$ transforms to Cb—Ft while an aldehyde such as $CH_3$—CH=O transforms to Cg=Ft and not Ak=Ft. See infra Cg and Ak. The acyclic noncarbon connecting group (Fc) is defined as a single atom that is neither carbon or hydrogen but may be attached to one or more hydrogens and must be attached to two or more other groups including itself, e.g., phenyl-O-phenyl is expressed as Cb—Fc—Cb. By definition, Fc may not stand by itself or attached to only one other group.

Figure 7:
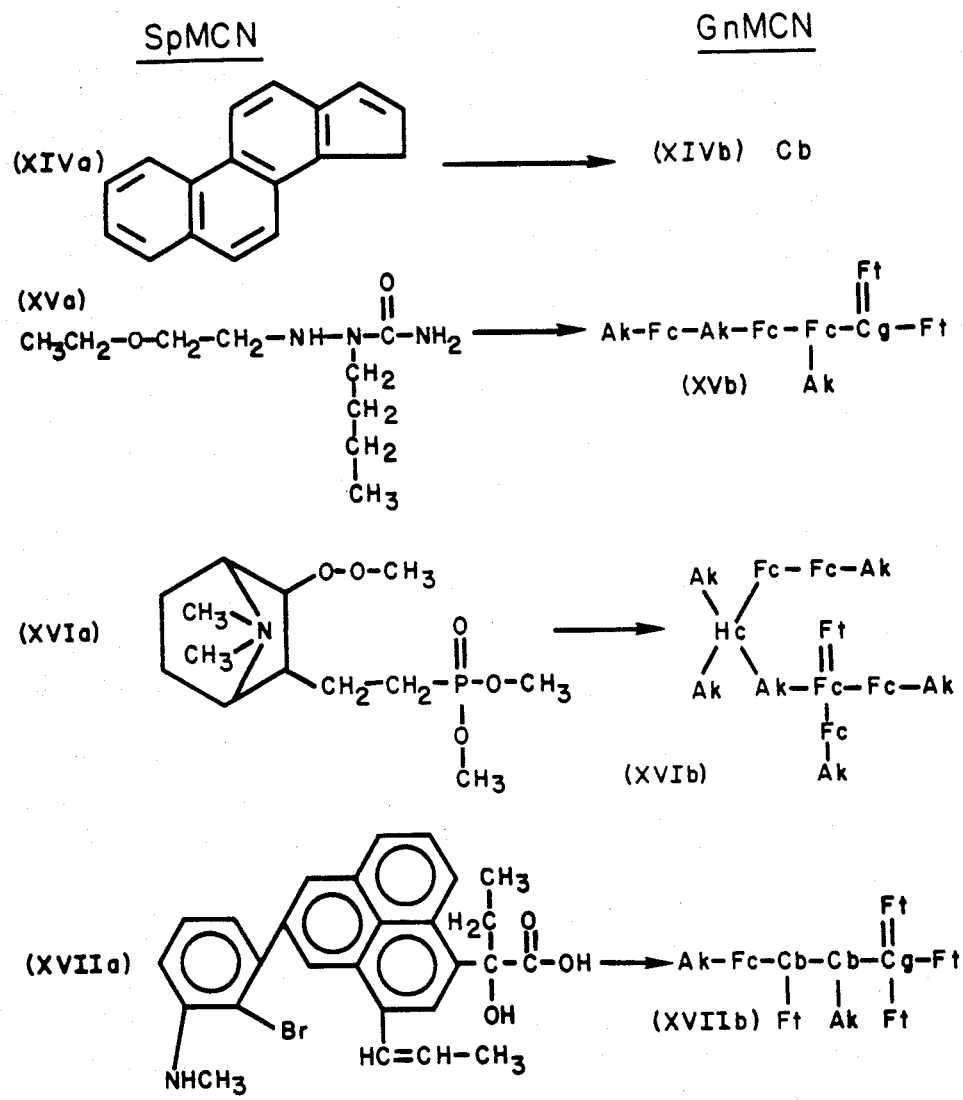
FIG. 7 illustrates the use of the hierarchical classification scheme in converting SpMCN to GnMCN structures.

The acyclic carbon group (Ch) is further broken down into an acyclic carbon group (Cg) attached to an acyclic noncarbon terminal group (Ft) by a multiple bond, or any other acyclic carbon group (Ak) not defined as Cg. By definition, the Cg group can not stand alone. It must be attached to at least one Ft group by a multiple bond and it may also be attached to other groups, except Ak or Cg. The Ak group consists of a group of acyclic carbon atoms and any attached hydrogen atoms that may stand alone or may be attached to any group, except Cg or Ak. When a Cg is attached to an Ak or another Cg or when an Ak is attached to a Cg or another Ak, the two groups merge into the appropriate single group, e.g., Ft=Cg—Cg=Ft becomes Ft=Cg=Ft, Ft=Cg—Ak becomes Ft=Cg, and Ak—Ak becomes Ak. $CH_3$—CH=O becomes Cg=Ft; $CH_3$—OH becomes Ak—Ft. The compound $CH_3$—$CH_3$ is not represented Ak—Ak but rather as simply Ak. The compound O=CH—$CH_2$C-$H_2$—CH=O is not represented as Ft=Cg—Ak—Ak—Cg=Ft but rather as Ft=Cg=Ft. Table I illustrates the hierarchical scheme using classification notation. FIG. 7 illustrates the use of the hierarchy to transform SpMCN representations to GnMCN representations.

TABLE I
Hierarchical Generic Group Classification

G any chemical group
Cy any cyclic group
Cb any all carbon cyclic group
Hc any cyclic group containing at least one noncarbon atom
Ay any acyclic group
Ch any carbon acyclic group
Cg any carbon acyclic group attached by a multiple bond to a terminal non-carbon acyclic group (Ft)
Ak any carbon acyclic group not defined by Cg
Fg any noncarbon acyclic group
Ft any noncarbon atom standing alone or attached to only one other group
Fc any noncarbon atom attached to two or more other groups The acyclic carbon group (Ak) can be further divided into two groups, one group in which at least one multiple carbon-to-carbon bond must be present and another group in which multiple carbon-to-carbon bonding is not allowed. Alternatively, the Ak group can be divided on the basis of the number of carbon atoms in the group. For a generalized file, separation into two groups in which one group contains six or fewer carbon atoms and another group containing more than six carbon atoms gives a relatively even number of file compounds to the two groups. Other groups, such as Cb and Hc can also be divided into more-specific, mutually-exclusive groups. E.g., Cb could be divided into fused and non-fused groups or into groups based on the number of rings within the group.

The above hierarchy is designed to meet the requirements of a search file consisting of a broad range of chemical compounds likely to be found in a broad definition of the chemical arts. However, this is not to imply that this invention is limited to this hierarchy since it is anticipated that other similar hierarchies may be defined to meet the needs of files limited to particular kinds of compounds, e.g., inorganic compounds, cyclic compounds, etc.

The classification hierarchy also is used to represent the generic language used in the original Markush formulation so as to enable the capture of this information in the SpMCN and GnMCN representations. For example, as seen in structure XVIIIa of FIG. 8, Markush formulations may contain terms that are in themselves generic, e.g., alkyl group, electron with-drawing group, and heterocyclyl. Because the hierarchy defines all possible chemical groups, generic terminology used in the Markush formulation can be captured and used in the matching process. For example, in going from structure XVIIIa to structure XVIIIb in FIG. 8, the alkyl becomes Ak, the electron-withdrawing group becomes the general group G, and the Heterocyclycl group becomes Hc. The appearance of generic groups from two sources in the GnMCN (structure XVIIIc), i.e., from the Markush formulation itself and from the real atoms in the SpMCN (structure XVIIIb) requires additional processing considerations if high levels of recall are to be obtained. To afford this additional processing, it is necessary to distinguish generic groups generated from real atoms from those generated from the original Markush formulation in the GnMCN representation. As shown in GnMCN representation XVIIIc, generic groups generated from the Markush formulation are designated with a prime (') to distinguish them from generic groups generated from the real atoms shown in structure XVIIIb.

FIG. 8 also illustrates other aspects of a Markush formulation that are anticipated by this invention. For example, the group $R_2$ is noted to have no specific point of attachment in the Markush formulation (XVIIIa) and in fact such formulation is intended to express the attachment of any of the groups designated by $R_2$ in any of the open positions on the six-membered ring. To handle such such a formulation, each of the $R_2$ groups is promulgated on each of the open nodes of the benzene ring in the SpMCN representation (XVIIIb). The use of "n" to express an alkyl chain of variable length in the Markush formulation (XVIIIa) is transformed to the SpMCN representation (XVIIIb) by separate expression of each unique moiety found in the "n" formulation. Finally it is noted that a Markush formulation may contain "limiting" logic, i.e., "If $R_1$=OMe, then $R_2$=Cl. Such "limiting" logic is associated and stored with the SpMCN representation and is verified after query SpMCN and file SpMCN matching is complete.

Figure 10:
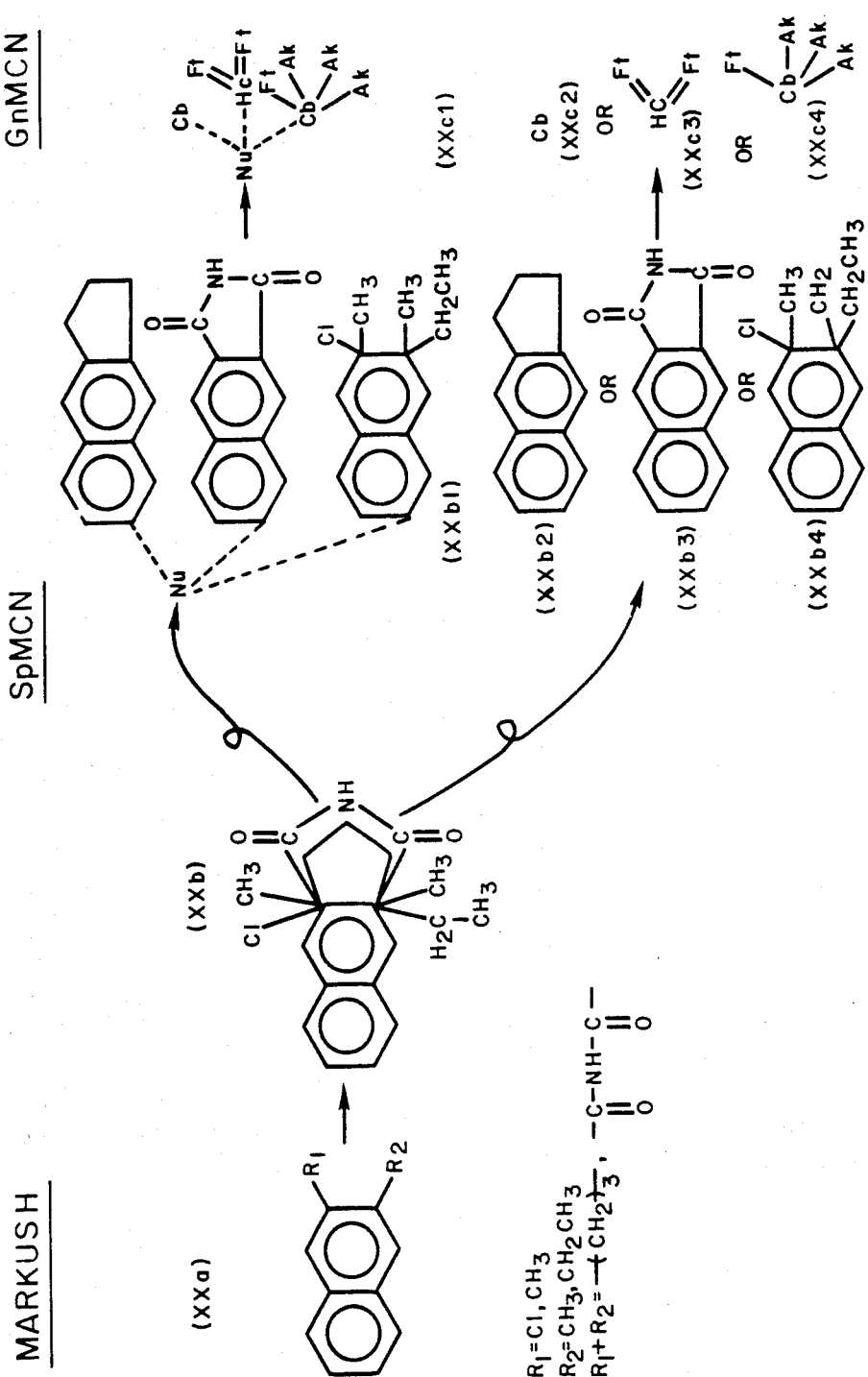
FIG. 10 illustrates simplification of complex features of the SpMCN and GnMCN by generation of a "null" point of attachment or use of Boolean logic.

In order to apply known structure matching techniques used for single compound matching to Markush searching in a straight-forward manner, it is necessary to simplify complex SpMCN and GnMCN structures that result from the representation of Markush formulations. Structure XIXb1 of FIG. 9 illustrates two such complexities, i.e., multiple ring formation when the point of variability is within a ring itself and the formation of "pseudo-rings" when the point of variability is within a chain structure. By moving the point of variability to a node (atom) outside of the ring, it is possible to eliminate such complex structural features (structures XIXb2 and XIXc). Occasionally, as shown in FIG. 10, the structural features of the SpMCN may not permit the shifting of the point of variability outside of the ring structure. This situation requires the use of a "null" or "dummy" node, or, alternatively, the use of Boolean logic to represent the various structural features. Representation XXb1 illustrates the use of the null node (Nu) while representations XXb2–XXb4 illustrate the use of individual representations linked by "OR" Boolean logic. The null node representation or Boolean logic representations are also used with the GnMCN representations (XXc1 and XXc2–XXc4, respectively).

One other feature that must be considered in the generation of the SpMCN and GnMCN is the concept of variable hydrogen ($H_v$). As was noted earlier, it is a common practice to disregard the presence of hydrogen in representing chemical structures, especially cyclic structures such as representations Ia1–Ia4 of FIG. 1, and, in fact, such a convention often is used in commercial structure-search systems. This is done typically to minimize storage requirements. The hydrogen atoms attached to carbon atoms are represented implicitly, i.e., the number of hydrogens attached to a carbon atom can be determined from the number of bonds and the number of non-hydrogen attachments. Although it is common notation to explicitly represent hydrogen in acyclic structures, such specific representation usually is not used in commercial structure search systems. Thus hydrogen is typically not explicitly used in either cyclic or acyclic structure search systems. See for example, "The CAS ONLINE Search System; General System Design and Selection, Generation, and Use of Search Screens" by P. G. Dittmar, N. A. Farmer, W. Fisanick, R. C. Haines, and J. Mockus (*J. Chem. Inf. Comput. Sci.*, 1983, 23, 93–102.), all of which is hereby incorporated by reference. However, in Markush formulations, hydrogen often is used as one of the fragments in a variable group, and, in order to achieve high recall, it is useful to express the hydrogen atom explicitly in such cases. For example, in Markush formulation XXIa of FIG. 11, the variable portion of the formulation contains the groups H, OH, and Cl. If the H is not recorded in the SpMCN and GnMCN, the basic ISSR, XXIb1, is "lost" to the implicit structure matching process at both the SpMCN and GnMCN levels. To avoid such a loss, the variable group hydrogen is explicitly represented in the SpMCN as $H_v$ so that the appropriate ISSR, XXIb1, can be anticipated in the SpMCN structure matching process. Likewise, variable hydrogen also is explicitly represented in the GnMCN representation so that the appropriate basic IGSR can be anticipated in the GnMCN structure matching process, e.g., ISSR, XXId1', of FIG. 11.

FIG. 11' illustrates the representation of $H_v$ and various combinations of generic groups that are forbidden by the classification scheme, e.g., Ak—Cg, Ak—Ak. In SpMCN representation XXIIb, $H_v$ is explicitly expressed. On transformation to the GnMCN representation XXIIc, several "forbidden" group combinations are observed, e.g., Ak—Cg, Ak—$H_v$, and Ak—Ak. These groups are appropriately combined according to the hierarchical rules to give the IGSRs, Ak(XIId1'), Cg=Ft(XXIId3'), and Ak—Fc—Ak(XXIId4'). Alternatively, the use of variable hydrogen in the GnMCN can be avoided by merging it with the $CH_2$ to give $CH_3$ and shifting the node of variability to the first carbon as shown in SpMCN representation XXIIe. It should be noted that the node of variability is shifted and not an individual substituent, i.e., if one substituent is shifted then all substituents must be shifted. The shifting of only one variable substituent of a set of variable substituents gives rise to extraneous structures not implicit in the original Markush formulation. SpMCN representation XXIIe is transformed to GnMCN XXIIf and the forbidden group combinations eliminated in the IGSRs.

Because of the broad nature of the hierarchical classification used in capturing the generic features of the original Markush formulation and in transforming the SpMCN representation to the GnMCN representation, considerable precision is lost in GnMCN structure matching if only the hierarchical groups are used to capture these generic features. For example, in FIG. 12, generic moieties a, b, and c and the specific moiety d represent varying levels of atom and bond specificity that are lost if such moieties are captured only as the generic group Hc. To improve GnMCN matching precision, attributes of any generic expressions from the original Markush formulation and real-atom moieties in the SpMCN are captured in an attributes table and used in an additional matching step immediately following the matching of a query and file group in query/file GnMCN structure match. Alternatively, attribute matching can be applied as a separate step following query/file GnMCN structure match for those cases where a structure match has been found. As shown in FIG. 12, suitable attributes for the Hc group are: (1) the identity of the hetero atom(s) and their number, (2) the size of the ring, and (3) the type of bonding in the ring. As shown in FIG. 12, moiety (a), heterocycle, conveys no additional attributes not found in the Hc group itself; moiety (b), N-heterocycle, conveys the fact that one or more of the heteroatoms (noncarbon atoms) in the heterocycle are nitrogen atoms; moiety (c), a 6-membered heterocycle, conveys the fact that there are six atoms in the cyclic structure, and (d), a specific atom structure, conveys the identity and exact number of heteroatoms (one nitrogen atom), the size of the ring (six atoms), and the number and type of bonds found in the cyclic structure (six normalized bonds). Attributes are derived from generic features described in the original Markush (moieties (a)–(c)) as well as from the specific atom structure found in the SpMCN representation (moiety (d)). The use of the attribute table in the query/file comparison process is illustrated in FIGS. 13 and 13' where the SpMCN, GnMCN, and Hc Attribute Table are given for file representations XXIII–XXV and query representation XXVI. FIGS. 13 and 13' illustrate a set of file compounds in which the IGSR XXVIb has been found to match at least one IGSR of each of the file representations (XXIIIb–XXVb). When a match between the Hc group in the query and the Hc group in the file representation is obtained during IGSR comparison, or alternatively in the step after GnMCN comparison, the query Hc attributes of the appropriate IGSR are compared with Hc attributes of the appropriate file IGSR. As is evident, the query Hc attributes XXVIc are included only within the file Hc attributes XXVc. Query attributes of the other groups making up the query IGSR also are compared with attributes of the corresponding groups of the file IGSRs. If all attributes of all groups of at least one query IGSR are included within all of the corresponding groups of at least one IGSR of a file GnMCN, the ISSRs of the associated query and file SpMCN representations are compared in the next step. In comparing attributes, only those attributes are compared for which a value exists in both the query and file list. If a particular attribute in either the query or file attribute list contains no information, no attempt is made to compare that particular attribute. Thus in comparing the query attribute list XXVIc with the file attribute list XXIVc, only attribute 1 (heteroatoms) was compared; no attempt was made to compare attributes 2 or 3. Depending on the precesion desired, additional detail can be used in describing a particular attribute. For example, if the attribute is derived from a real-atom configuration it is typically a closed set, i.e., limited to a specific value, while an attribute derived from a generic term may be an open set where additional or alternate values are possible. If attribute 1 of file representation XXIVc is considered as an alternate expression, i.e., one or more nitrogen or one or more oxygen atoms, then the query attributes XXVIc would also be included within its attributes. Such level of detail in attribute description is typically handled by using the appropriate Boolean logic.

FIGS. 2-4 illustrate the general search strategy of this invention, i.e., matching of IGSRs followed by matching of ISSRs. The IGSRs of FIGS. 3 and 3' and the ISSRs FIG. 4 were developed on the basis of an intuitive logic, i.e., following from the Markush formulation itself. Although the development of the ISSRs of FIG. 4 is aided significantly by the fact that each ISSR must follow the usual connectivity rules of the chemical arts, at the generic level, such connectivity rules are no longer available for the development of IGSRs. One approach to the problem is to break the query GnMCN into its simplest structural units and compare these units with the file GnMCN representations. Thus in FIG. 3', query representation VIIc breaks down into carbocycle-halide and carbocycle-alkyl. Comparing either of these groups with the file GnMCN representations results in all but structure IVc giving a match. At this point, two things are noted: (1) it is not necessary to generate the implicit file GnMCN structures—the GnMCN structure itself can be used to see if the fragment is contained within the structure, and (2) by using a less specific implicit query representation, an additional answer, irrelevant to be sure, is obtained, i.e., representation IIIc. Representation IIIc does, of course, drop from the search at the SpMCN level of matching.

In order to obtain the highest level of specificity for the ISSRs and IGSRs implicit in the respective SpMCN and GnMCN structures and to obviate the need to expand each file and query SpMCN and GnMCN structure into its respective ISSRs and IGSRs, it is highly desirable to have an indexing system that allows for the recognition of all ISSR and IGSRs within the respective query and file SpMCN and GnMCN structures. Such an indexing system is illustrated in FIG. 14. Each atom and group is assigned a "flag" ($f_n$) that indicates the level of variability (zero level in the case of atoms or groups in the base structure) and, if appropriate the k value of the substituent, i.e., $r_k$. As seen in Table II, such an indexing system makes it possible to easily track all possible combinations of the substituent groups.

One possible isolation scheme is to first select a fragment in a variable group of the first level of variability, for example, Br ($r(1)f(1)$) and then "prune" or discard other alternative fragments in the same variable group and take all but one fragment in any other variable group as denoted by the appropriate flags. Such a procedure leads directly to a single ISSR or IGSR structure. By keeping track of which fragments have been used, all ISSRs or IGSRs of the respective SpMCN or GnMCN representation can be generated.

TABLE II

| f(0) | r(1)f(1) | r(2)f(1) | f(3)f(2) |
|---|---|---|---|
| ISSRs | | | |
| Base structure | Br | N(CH3)2 | — |
| Base structure | Br | NHCH2CH2 | OCH3 |
| Base structure | Br | NHCH2CH2 | SCH3 |
| Base structure | Cl | N(CH3)2 | — |
| Base structure | Cl | NHCH2CH2 | OCH3 |
| Base structure | Cl | NHCH2CH2 | SCH3 |
| Base structure | OCH3 | N(CH3)2 | — |
| Base structure | OCH3 | NHCH2CH2 | OCH3 |
| Base structure | OCH3 | NHCH2CH2 | SCH3 |
| IGSRs | | | |
| AkHc | Ft | FcAk2 | — |
| AkHc | Ft | FcAk | FcAk |
| AkHc | Ft | FcAk | FcAk |
| AkHc | Ft | FcAk2 | — |
| AkHc | Ft | FcAk | FcAk |
| AkHc | Ft | FcAk | FcAk |
| AkHc | FcAk | FcAk2 | — |
| AkHc | FcAk | FcAk | FcAk |
| AkHc | FcAk | FcAk | FcAk |

In its most basic form, such an index system requires that all r(k) values be different. Thus in representation XXVIIc, the generation of an implicit structure with two Ft groups attached to Hc is forbidden, since such a structure would have two r(1) groups. The index system can also be used to handle complex Markush formulations by using the node flags as a way of breaking down a complex structure into separate structures linked by appropriate Boolean logic. In such a treatment, it is necessary to capture some atom and group detail from the previous and next higher level of representation so as to preserve suitable detail for atom and group matching techniques.

In capturing as much detail of the Markush formulation as possible, generic features of the Markush formulation are captured in the SpMCN representation as generic groups, e.g., representation XVIIIb of FIG. 8. The use of such generic features in the SpMCN representation can result in a matching failure if appropriate steps are not taken to allow for this situation at the SpMCN matching level. To allow for appropriate generic group matching at the SpMCN matching level, "roll-back" to the associated GnMCN level of representation is used. The "roll-back" technique is illustrated in FIG. 15. The query SpMCN representation XXVIIIa of FIG. 15 contains a phenyl group (uppermost portion of the representation) that is implied in the generic group Cb of the file compound XXIXa (uppermost portion of the representation).

Atom-by-atom structure matching will fail to match these two terms since the query segment contains carbon atom (C) nodes which do not match with the generic group (Cb) node. On identification of a mismatch due to a comparison of a real atom node against a generic group node (as noted earlier, generic groups in the SpMCN representation are distinguished by a prime (') since they must originate from a generic feature in the Markush formulation; alternatively, such generic groups can be identified through a table lookup), the appropriate real-atom part of the query (or file) substance is rolled-back to its associated generic group node and the two generic group nodes are compared. Thus, in the example, the real-atom carbon atoms are rolled-back to the generic group node Cb and the Cb node used to match the Cb node in the file representation. In the second segment of the molecule, the query contains a generic feature (Ak) while the file compound contains real atoms (CH₂CH₂). In this case, the file segment is rolled back to the generic group (Ak) and Ak used in the matching process.

In using generic groups, one additional factor must be considered. For example, in FIG. 15 the middle segment of the query (Ak) was successfully compared with the rolled-backed Ak segment of the file group. If the query segment had been a Ch group instead of an Ak group, a match would not have been obtained even though, by hierarchical group definition, the Ak group is included within the definition of a Ch group. To account for such generic mismatch at either the GnMCN/GnMCN matching level itself or on roll-back to the GnMCN group level in SpMCN/SpMCN matching, a particular group within the hierarchy is expanded to include as alternate node values all groups above it in the hierarchy (thus expanding Ch to include Ay and G) and all lower lower groups in the hierarchy (Cg and Ak). By using such an expansion for all file generic groups, a generic group node, such as Ch or Ay, in the query will successfully match an expanded Ak group node in the file substance and vice-versa.

Although the use of GnMCN representation matching and GnMCN attribute matching reduces the amount of SpMCN representation matching considerably, it is of further advantage to eliminate from the file as many irrelevant GnMCN and SpMCN structures as possible prior to GnMCN group-by-group and SpMCN atom-by-atom matching since these latter two processes are relatively slow even when using high-speed computers. Such a reduction in file size is accomplished by use of a modified version of known screening techniques such as those described in "The CAS ONLINE Search System; General System Design and Selection, Generation, and Use of Search Screens" by P. G. Dittmar, N. A. Farmer, W. Fisanick, R. C. Haines, and J. Mockus (*J. Chem. Inf. Comput. Sci.*, 1983, 23, 93–102.), all of which is hereby incorporated by reference. The generation of specific-atom screens, generic group screens, and diagnostic screens is illustrated in FIG. 16. Specific atoms screens are illustrated with representation XXXa of FIG. 16. Augmented Atom (AA) screens are defined as screens involving an atom and its nearest neighbor atoms and the attaching bonds. For example, in a first ISSR of XXXa (ISSRs are not explicitly shown), the first carbon atom (C) is attached to only one other carbon by a single bond (hydrogen atoms being ignored). The second carbon is attached to the first carbon and a third carbon; the third carbon is attached to the second carbon and an oxygen (O); and the oxygen is attached to a carbon. In a second ISSR of XXXa, the first carbon is attached to one other carbon, the second carbon is attached to the first carbon and to a third carbon, the third carbon is attached to the second carbon and to a nitrogen (N), and the nitrogen is attached to the third carbon. In a third ISSR, the first carbon is attached to the second carbon and the second carbon is attached to the first carbon and a third carbon, and the third carbon is attached to the second carbon; generic groups are specifically ignored in the generation of real atom screens. The general notation for AA screens is to cite the atom under consideration first followed by each attached atom in alphabetical order with the bonding immediately preceding each attached atom.

Another type of screen is the Atom Sequence (AS) screen in which linear sequences of four to six nonhydrogen atoms are described. For the ISSRs of XXXa, there are two four-atom sequences, C—C—C—N and C—C—C—O. A third type of screen is the Element Count (EC) screen which indicates the presence of specific elements and for some of the more common elements, a count of the number of atoms, e.g., six or more carbon atoms.

After generating the AA, EC, and AS screens, they are looked up in a screen dictionary (Table III) to obtain their corresponding screens numbers. The screen numbers correspond to specific bits in a bit string illustrated in FIG. 16. It is noted that in screen fragment generation, larger fragments are decomposed into smaller, more generic screen fragments that are also included in the screen dictionary. For example, the AA screen fragment, C—C—O (#4), is decomposed into C—C (#1) and C—O (#6). As illustrated in FIG. 16, the screens for the three ISSRs of the SpMCN representation XXXa turn on bits 1, 2, 4–7, 11–13, 17, and 19.

TABLE III

SCREEN DICTIONARY
SPECIFIC ATOM SCREENS

| | SCREEN NUMBER |
|---|---|
| EC SCREENS | |
| C | 11 |
| O | 13 |
| N | 12 |
| Cl | 14 |
| AA SCREENS | |
| C—C | 1 |
| Cl—C | 9 |
| N—C | 7 |
| O—C | 6 |
| C—C—C | 2 |
| C—C—Cl | 10 |
| C—C—N | 5 |
| C—C—O | 4 |
| C—C—C—C | 3 |
| C*C*C | 8 |
| C*C | 15 |
| AS SCREENS | |
| C—C—C—C | 18 |
| C—C—C—Cl | 20 |
| C—C—C—N | 19 |
| C—C—C—O | 17 |

(— indicates a chain bond; * indicates a ring bond)

TABLE IV

SCREEN DICTIONARY
GENERIC SCREEN

| SCREENS | SCREEN NUMBER |
|---|---|
| Ak | 58 (51,57,59) |
| Ak-Ay | 37 (36,42,43,46,47,48; 51,57,58,59) |
| Ak-Cb | 34 (33,36,43,46,48,49,50,60,61,62; 51,52,53, 57,58,59) |
| Ak-Cy | 33 (36,43,46,48,49,50,60; 51,52,57,58,59) |
| Ak-Fg | 32 (36,37,41,42,43,44,45,46,47,48; 51,56,57,58,59) |
| Ak-Ft | 31 (32,36,37,38,39,40,41,42,43,44,45,46,47,48; 51,55,56,57,58,59) |
| Ak-G | 36 (43,46,48; 51,57,58,59) |
| Ak-Hc | 35 (33,36,43,46,48,49,50,60,63,64,65; 51,52,54, 57,58,59) |
| Ay | 57 (51) |
| Ay-Ay | 47 (46,48; 51,57) |
| Ay-Cb | 62 (46,48,50,60; 51,52,53,57) |
| Ay-Ch | 42 (43,46,47,48; 51,57,59) |
| Ay-Cy | 50 (46,48,60; 51,52,57) |
| Ay-Fg | 44 (45,46,47,48; 51,56,57) |
| Ay-Ft | 39 (40,45,46,47,48; 51,55,56,57) |
| Ay-G | 48 (46; 51,57) |
| Ay-Hc | 64 (46,48,50,60,63; 51,52,54,57) |
| Cb | 53 (51,52) |
| Cb-G | 63 (46,60; 51,52,53) |
| Ch | 59 (51,57) |
| Ch-Cb | 61 (43,46,48,49,50,60,62; 51,52,53,57,59) |
| Ch-Cy | 49 (43,46,48,50,60; 51,52,57,59) |

TABLE IV-continued
SCREEN DICTIONARY
GENERIC SCREEN

| SCREENS | SCREEN NUMBER |
| --- | --- |
| Ch-Fg | 41 (42,43,44,46,47,48; 51,56,57,59) |
| Ch-Ft | 38 (39,40,41,42,43,44,46,47,48; 51,55,56,57,59) |
| Ch-G | 43 (46,48; 51,57,59) |
| Ch-Hc | 65 (43,46,48,49,50,60,63,64; 51,52,54,57,59) |
| Cy | 52 (51) |
| Cy-G | 60 (46; 51,52) |
| Fg | 56 (51,57) |
| Fg-G | 45 (46,48; 51,56,57) |
| Ft | 55 (51,56,57) |
| Ft-G | 40 (45,46,48; 51,55,56,57) |
| G | 51 |
| G-G | 46 (51) |
| G-Hc | 63 (46,60; 51,52,54) |
| Hc | 54 (51,52) |

TABLE V
SCREEN DICTIONARY
DIAGNOSTIC SCREENS

| SCREENS | SCREEN NUMBER |
| --- | --- |
| Ak' | 78 (71, 77, 79) |
| Ay' | 77 (71) |
| Cb' | 73 (71, 72) |
| Ch' | 79 (71, 77) |
| Cy' | 72 (71) |
| Fg' | 76 (71, 77) |
| Ft' | 75 (71, 76, 77) |
| G' | 71 |
| Hc' | 74 (71, 72) |

For illustrative purposes, the screens and Specific-Atom Bit String used to depict the ISSRs of SpMCN representation XXXa have been simplified extensively. This is in no way intended to limit this invention to this particular description; various other screens described in the article by Dittmar, et. al, ibid, e.g., bond sequences, atom counts, etc. used for specific-atom screening are also anticipated by this invention.

In developing screens for the GnMCN representation, it typically is not necessary to generate as wide an array of screens as is used with the SpMCN representation since many of the atomic features of the SpMCN representation are compressed into a single group in the GnMCN representation. Typically, AA doublets or dumbbells (a generic group joined to one other generic group) and singlets (a generic group by itself) are adequate for satisfactory screening at the generic group level. As with the specific atoms screens, this description is given in simplified form to teach the invention and is not intended to limit the number or types of screens used for generic group screening.

The GnMCN representation XXXb contains two dumbbell screens, Ak—Ft and Ak—Cy. Since Ak—Cy implies the more specific screens, Ak—Cb and Ak—Hc, these screens must also be included as possible screens and are generated at the time of bit string construction. If these two more specific screens are not included, this particular file compound would be screened out when in fact it is a potential match for a query such as Ak—Hc, i.e., the query alkyl-heterocycle (Ak—Hc) is implicit in the file alkyl-cyclic group (Ak—Cy). In examining the screen dictionary given in Table IV, it is apparent that the Generic-Group screens, contain the more generic screens for that screen. Thus the screen Ay—G includes the more generic doublet term G—G and the singlets, Ay and G. As a result, the screen dictionary automatically accounts for the matching of related, but more generic fragments in which the more specific fragment is contained. For generic representation XXXb, bits 31-33 and 36-65 are turned on in the Generic-Group Bit String.

For generic groups that originate from generic expressions in the original Markush formulation and, as noted in FIG. 8, denoted with a prime, a special diagnostic bit screen is used. As with the generic screens, the more generic terms are included with the term in the diagnostic screen dictionary (Table V), e.g. Cy' includes G,; more specific terms are generated at the time of bit string construction, e.g., Cb' and Hc' are generated for Cy'. As a result, bits 71-74 are turned on in the Diagnostic Bit String illustrated in FIG. 16.

In bit string generation for both generic and specific atom file representations, screens for all possible ISSRs and IGSRs are included in a single bit string. Moreover, the specific screens are generated without a consideration of the boundaries which result when real atoms are transformed into generic groups. Thus in representation XXXa of FIG. 16, the AA screen C—C—O (No. 4) involved atoms (C—C) that transformed into the Ak group and an atom (O) that transformed into the Ft group.

For query representations, each ISSR is considered as a separate entity and real-atom screens are generated so as to restrict the real atoms screens to atoms that transform to a single generic group or generic-group combination. To simplify the illustration of the screening technique, the real-atom screens are restricted to the boundaries of a single generic group but this is not intended to restrict the scope of the invention. Although real-atom screens must be restricted to the boundaries or the corresponding generic counterpart, the generic counterpart may be defined by any number of generic-group combinations. In representation XXXIa of FIG. 17, the real atom screens are limited to those atoms that transform to a single group, i.e., the screens are derived from three disconnected fragments, $CH_3CH_2CH_2$, Cl, and OH. Only the AA screens C—C—C and C—C are used for the group $CH_3CH_2$. AA screens, C—C—Cl and C—C—O, and AS screens, C—C—C—Cl and C—C—C—O, are not used since these screens span two separate generic groups. Correspondingly, the diagnostic generic screens are limited to the singlets, Ak and Ft.

Query XXXIa FIG. 17 along with the Specific-Atom and Generic Group Bit Strings of FIG. 16 illustrate the screening technique in its basic form. The IGSR Ak—Ft of XXXIb, corresponding to ISSR $CH_3CH_2CH_2Cl$, gives rise to two disconnected singlets, Ak and Ft, which have corresponding screen numbers 51, 55, 56, 57, 58, and 59. Using Boolean logic, the query bit requirement is expressed as (Ak: 58 OR 51 OR 57 OR 59) AND (Ft: 55 OR 51 OR 56 OR 57). (The Ak and Ft in the logic expression are present for illustrative purposes only.) Examining the file Generic-Group Bit String in FIG. 16, this initial condition is met. Proceeding to the ISSRs, query ISSR $CH_3CH_2CH_2Cl$, which is treated as two disconnected fragments, $CH_3CH_2CH_2$ and Cl, requires that the file Specific-Atom Bit String contain the following Boolean logic query: 1 And 2 And 11 And 14. In examining the file Specific-Atom Bit String of FIG. 16, it is apparent that this logic condition is not met since bit 14 is off.

Proceeding to the next implicit structure (as is recalled only one implicit structure of the query must match with an implicit structure of the file representation), IGSR of $CH_3CH_2CH_2OH$ is the same as that for CH₃CH₂CH₂Cl, i.e., Ak—Ft, and thus it must also match the Generic-Group Bit String of FIG. 16. The Boolean logic query expression 1 And 2 And 11 And 13 is obtained for the ISSR, CH₃CH₂CH₂OH, as the disconnected fragments CH₃CH₂CH₂ and OH, and is found in the Specific-Atom Bit String of FIG. 16. Since both the generic-group and specific-atom logic expressions of at least one IGSR and corresponding ISSR of query XXXI is found in the file Generic-Group and Specific-Atom Bit Strings, the associated GnMCN and SpMCN representations are then compared using group-by-group and atom-by-atom techniques for each IGSR and ISSR of both the file and query GnMCN and SpMCN representations. Unlike group-by-group and atom-by-atom matching, which requires that each IGSR and ISSR of both the file and query GnMCN and SpMCN representations be compared, screening is satisfied as long as the generic-group and corresponding specific-atom screens of at least one IGSR and corresponding ISSR is found in each aggregate file Generic-Group and corresponding Specific-Atom Bit String, i.e., screens from all IGSRs and ISSRs for each file GnMCN and and associated SpMCN representation.

ISSRs XXXIIa and XXXIIb of FIG. 17 illustrate the handling of a generic feature found in the original Markush formulation. Look-up of the individual generic groups of XXXIIb in the generic screen dictionary (Table IV) results in the logic expression, (Ak: 58 OR 51 OR 57 OR 59) AND (Hc: 54 OR 51 OR 52) which is found in the Generic-Group Bit String of the file representation of FIG. 16. In formulation a logic expression for an ISSR, all generic groups are ignored. As a result, ISSR XXXIIa corresponds to the fragment CH₃CH₂CH₂ and results in the logic expression, 1 AND 2 AND 11, which is also found in the Specific Bit String shown in FIG. 16. IGSR XXXIIb also illustrates the need to expand file representations to include all more specific members, i.e., Ak—Cb and Ak—Hc in representation XXXb. If the file representation had not been expanded to include these members of the generic group, IGSR XXXIIb would have failed to match.

ISSR XXXIIIa and IGSR XXXIIIb of FIG. 17 illustrates the use of the file Diagnostic Bit String (FIG. 16) in handling a real-atom segment in the query ISSR when the corresponding file ISSR has only a generic group corresponding to that segment as a result of originating in a generic feature of the original Markush for which no real-atom structure information is available. The individual generic groups of IGSR XXXIIIb give rise to the logic expression, (Ak: 58 OR 51 OR 57 OR 59) AND (Cb: 53 OR 51 OR 52) which is found in the Generic-Group Bit String of the file representation XXXb. The specific atom groups of ISSR XXXIIIa give rise to the logic expression, 1 AND 2 AND 8 AND 15. The logic expression does not match with the file Specific-Atom Bit String of FIG. 16 since bits 8 and 15 of the file Bit String are off. However, it is noted that the file ISSR CH₃CH₂CH₂Cy does match the query ISSR. The failure to recognize the match results from the fact that the query ISSR contains a real-atom three-carbon ring-system from which the screen fragments C*C (#15) and C*C*C (#8) are derived while the file ISSR contains a generic group Cy from the original Markush formulation for which the screen fragments C*C and C*C*C are not generated. In order to insure that the file substance is not missed, the diagnostic screens exist in the file Diagnostic Bit String to indicate when alternatives to real-atom query screens must be used, i.e., they indicate when there are no real-atom screens in the file Specific-Atom Bit String for a particular segment of the file representation. (This is done since it is not practical to generate and include in the Specific-Atom Bit String all possible real-atom screens that correspond to the various generic groups.) For example, the generic group corresponding to the query cyclic group in representation XXXIIIa is Cb. On examining the diagnostic bit string for file representation XXXa (FIG. 16), the diagnostic bit for Cb (#73) is "on". As stated, the fact that the diagnostic screen is on for Cb means that the Cb group originated from a generic feature of the Markush formulation and, as such, no corresponding real atom screens are available in the file Specific-Atom Bit String for this group. To obtain a match with this file representation, it is necessary to use as an alternative to the real-atom screens corresponding to Cb in the query logic expression the diagnostic screens 73 OR 71 OR 72. As a result, screens 8 and 15 are not required to be present for file representation XXXa if one of the above mentioned diagnostic screens is present, and the resulting "reduced" real-atom screen query logic expression for XXXIIIa is (1 AND 2 AND 11) AND ((8 AND 15) OR (Cb': 73 OR 71 OR 72). Since this expression matches the Specific-Atom and Diagnostic Bit Strings of FIG. 16, the file representation of FIG. 16 becomes a candidate for GnMCN group-by-group and SpMCN atom-by-atom matching. As has been seen, the purpose of the file diagnostic screens is to provide the necessary alternative to specific-atom screens in the query logic expression when the file representation contains no real-atom screens against which the specific-atom screens of the query expression can match. The function of this special Boolean strategy is to insure as high a recall as possible for the system.

For illustrative purposes, generic acid specific query/file screen matching has been detailed in three steps, i.e., (1) matching of a generic query logic expression with the generic file bit string (2) matching of a specific query logic expression with a specific file bit string, and, (3) using alternative diagnostic screens for specific-atom query screens when the appropriate diagnostic screens are present in the file Diagnostic Bit String. In practice, all three steps can be combined. A single specific and generic logic expression is formulated for all segments of the ISSR and within the specific logic expression diagnostic screens are used as alternatives for the appropriate sets of real-atom screens that have been derived from fragments corresponding to individual generic groups. Thus the complete logic expression for implicit representations XXXIIIa and XXXIIIb is: (((1 AND 2 AND 11) OR (Ak': 78 OR 71 OR 77 or 79)) AND (Ak: 58 OR 51 OR 57 OR 59)) AND ((1 AND 8 AND 15) OR (Cb': 73 OR 71 OR 72) AND (Cb: 53 OR 51 OR 52)). This expression is passed against a combined Specific-Atom, Generic-Group, and Diagnostic Bit String in one step with the appropriate diagnostic screens being used according to their presence in the combined file Bit String. Moreover, complete logic expressions for all ISSRs and IGSRs in a single SpMCN and associated GnMCN query can be combined into a single logic expression. Thus for SpMCN, XXXIa, and associated GnMCN, XXXIb, the following logic expression is obtained: (((1 AND 1 AND 11) OR (Ak': 78 OR 71 OR 77 OR 79)) AND (Ak: 58 OR 51 OR 57 OR 59)) AND (((13 OR 14) OR (Ft': 75 OR 71 OR 76 OR 77)) AND (Ft: 55 OR 51 OR 56 OR 57)).

In formulating specific atom screens, it is essential to limit specific atom screens to the specific atoms defined by generic groups. As is apparent, this specific atom screen limitation is necessary so that a specific-atom group in a query can match a corresponding generic group in the file that has no real-atom counterparts using the Boolean strategy involving diagnostic screens. For illustrative purposes, the boundaries for real-atom screens have been limited to to a corresponding single generic group. In practice, combinations of generic groups are defined and all real-atom screens within the generic-group combination used. For example, the real-atom screens corresponding to the generic-group pair combination Ak—Ft can be for the ISSR $CH_3CH_2CH_2Cl$ of representation XXXIa of FIG. 17. In such a situation, the AA real-atom screen C—C—Cl (#10) and AS screen C—C—C—Cl (#20) are used to eliminate additional irrelevant structures from the file, i.e., to improve search precision. However, in using such screens, the diagnostic screen boundaries must be expanded by using the pair combination set Ak′—Ft, Ak—Ft′, and Ak′—Ft′, i.e., Ak′—Ft OR Ak—Ft′ OR Ak′—Ft′ as alternatives for the real-atom screen set. To afford even greater precision, both generic group pairs and singlets can be used as diagnostic screens. For example, if the real-atom screens derived from $CH_3CH_2CH_2Cl$ are denoted as "set a", the screens from $CH_3CH_2CH_2$ as "set b", and the screens Cl as "set c", and the diagnostic screens are Ak′, Ft′, and (Ak′—Ft OR Ak—Ft′ OR Ak′—Ft′); then the logic expression is ((set a OR (Ak′—Ft OR Ak—Ft′ OR Ak′—Ft′) AND (set b OR Ak′) AND (set c OR Ft′)). The "set a" screens are not used against a file substance with a GnMCN containing Ak′—Ft, Ak—Ft′, or Ak′—Ft′, i.e., a GnMCN associated a SpMCN which has an Ak′ attached to a real-atom group corresponding to a Ft, a Ft′ attached to a real-atom group corresponding to an Ak, or a Ak′—Ft′.

Alternative to the above technique, an inverted file technique can be used for the storage and searching of the file substance screens rather then bit strings. In this technique, the screens (specific-atom, generic group, and diagnostic) become file index terms and a common identifier for the GnMCN and SpMCN representations associated with a given screen are "inverted" under the file index term. The query screen logic expression is developed in the same manner as for bit-string searching and is processed against the screen index file giving as answers those substance identifiere having the requisite query screens.

identifiers. Each file identifier is posted under the corresponding screens generated from the SpMCN and GnMCN representation. Appropriate file identifiers meeting the requisite Boolean logic conditions of the query logic expression are retrieved as answers, here, file identifiers "B" and "E." These GnMCN and SpMCN representations associated with the answers are then further processed in group-by-group and atom-by-atom searching.

FIG. 18 illustrates the general operation and computer hardware facilities for the practice of this invention. A user terminal such as a Hewlett-Packard 2647A (Hewlett-Packard Co., Cupertino, CA) is used for graphic structure input. Query and search control uses the resources of a large computer system such as one or more IBM 3081s (IBM Corp., Poughkeepsie, NY) and includes a telecommunications interfact and query and search control procedures such as those described in Zeidner, C. R.; Amoss, J. O.; Haines, R. C. "The CAS ONLINE architecture for Substructure Searching" in "Proceedings of the 3rd National Online Meeting" Learned Information, Inc.: Medford N.J., 1982; all of which is incorporated herein by reference, software for handling graphic structure input such as the Online Structure Input System (OLSIS: J. E. Blake, N. A. Farmer, and R. C. Haines. "An interactive Computer Graphics System for Processing Chemical Structure Diagrams." *J. Chem. Inf. Comput. Sci.*, 1977, 17, 223–228), all of which is herein incorporated by reference, a data-base management program such as ADABAS (Software AG, Darmstadt, W. Germany) used during answer data retrieval to access data bases such as patent files, abstracts files, etc., and output programs for online answers and off-line prints through a high-speed printer such as the Xerox 9700 laser printer (not shown; Xerox Corporation, El Sequndo, CA). Initial screen search is performed on a set of minicomputers such as Digital Equipment Corp. (Maynard, MA.) PDP11/45s while group-by-group and atom-by-atom searches and logic condition verification are carried out on a set of minicomputers such as Digital Equipment Corp. PDP 11/44s with one or more microcomputers such as the Digital Equipment Corp. PDP 11/55 and PDP 11/44 used for system support, maintenance, and backup.

In a typical search, a screen logic expression is formulated from the query GnMCN and SpMCN structures and includes a special Boolean strategy to ensure retrieval of all representations based on generic representations in the original Markush formulation and is

TABLE VI

| INVERTED SCREEN FILE SCREENS | | | | | | | | | | | | | | | | | | | |
|---|---|---|---|---|---|---|---|---|---|---|---|---|---|---|---|---|---|---|---|
| Real Atom | | | | | | | | | | Generic Group | | | | | | | Diagnostic | | | |
| 1 | 2 | 3 | 4 | 5 | 6 | 7 | 8 | 9 | 10 | 41 | 42 | 43 | 44 | 45 | 46 | 47 | 70 | 71 | 72 | 73 |
| A |   |   | A | A | A |   | A |   |   |   |   | A |   | A | A | A |   |   |   |   |
| B | B |   |   |   |   |   |   |   |   | B | B | B |   |   |   |   | B | B |   |   |
|   |   | C | C | C | C |   |   | C |   |   |   | C | C |   |   |   | C |   |   | C |
|   | D |   |   |   |   |   | D | D |   |   |   |   |   | D |   |   | D | D |   |   |
| E | E | E | E |   | E | E | E | E |   |   | E | E | E |   | E |   |   | E |   | E |

QUERY: ((2 AND 3) OR (71 OR 72)) AND (41 OR 43)

For example, in Table VI, "A" is the identifier for a file SpMCN and associated GnMCN representations from which real-atom, generic-group, and diagnostic screens are derived. "B" is the identifier for another file SpMCN and associated GnMCN from which real-atom, generic-group, and diagnostic screens are derived. "C," "D," and "E" are similar file representation passed against the bit screen files. Answers from the screening search are passed to generic group-by-group search to determine if any IGSRs in the query GnMCN representation are found in the file GnMCN representations. Attributes of each generic-group node of the query representation are compared with the attributes of each matching generic-group node of the file representations during the GnMCN comparison. File answers from the generic-group/attribute match are passed to an atom-by-atom search to determine if any ISSRs in the query SpMCN representation are found in the file SpMCN representations. A roll-back technique is used to achieve a high degree of recall during atom-by-atom comparison by substituting a corresponding generic-group node for a real-atom group of nodes when such a generic group node occurs in the query or file substance. Resulting answers are checked to confirm that all substituent logic conditions are met. The answers are returned to query control where answers from appropriate data bases are retrieved and forwarded to the user along with the substance search answers.

APPLICABILITY

This invention provides a powerful tool for Markush structure storage and searching. It is designed to achieve total recall and very high precision for the searching of Markush-type queries against a file of generic substances of the type found in Markush patent claims. The query and file representations handled range from specific structures to those with high variability and generic features, including those that consist solely of generic features. Both full-structure and substructure searching, at both the specific-atom and generic-group level afford a wide range of search capability.

A single multiple connectivity node structure for specific-atom representations and an associated single multiple connectivity node structure for generic-group representations afford a manageable file size for the Markush formulations. An indexing system for for both the specific-atom and generic-group multiple connectivity node structures assures the generation and processing of all implicit structures within the generic-group and specific-atom multiple connectivity node structures as well as providing for a means of dealing with highly complex structures.

A hierarchical generic-group classification scheme provides a means for the input of generic features for both generic and file substances and, more importantly, provides a controlled language for the fail-safe matching of generic groups against generic groups and real-atom groups against generic groups. This is accomplished by mapping all groups, both real-atom and generic groups in the query and file substances, to a common set of generic groups as defined by the hierarchy which can be dealt with by the search routines, especially the initial screening step.

A screening technique is used to reduce the number of irrelevant file answers for a particular query on a rapid and "fail-safe" basis. The fail-safe result is achieved through a built-in handling of the generic vs. generic and real-atom vs. generic matching via the common set of generic groups as defined by the hierarchy. Real-atom screens are used to improve precision in the screening process and, in order to preserve a high level of recall, alternative Boolean diagnostic screens are provided in the query screen logic expression for use when certain real-atom screens are not appropriate.

High precision is achieved by matching file and query substances on a group-by-group and atom-by-atom basis. This type of matching establishes the required connectivity and arrangement of matching fragments lacking in presently available systems. Attribute searching provides added precision to the group-by-group by requiring that the attributes of two matching groups also match. In atom-by-atom matching, a roll-back technique is used to allow for the matching of a generic feature expressed as a generic group in the query or file substance to match against a corresponding real-atom group in the query or file substance.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

What is claimed is:

1. A method for storing and searching Markush formulations using a programmable digital computer system and comprising:
   a. forming in said digital computer system a file from a plurality of Markush formulations wherein each said Markush formulation is stored;
      (1) as a specific multiple connectivity node (SpMCN) representation of all implicit individual specific structural represenations (ISSRs) of each said Markush formulation,
      (2) as an associated generic multiple connectivity node (GnMCN) representation of all implicit individual generic structural representations (IGSRs) of each said Markush formulation, and
      (3) with associated reference data,
   b. comparing in said digital computer system each IGSR of a GnMCN representation of a query Markush formulation with each said IGSR of said file GnMCNs to give a set of file GnMCN answers in which at least one said IGSR of each said file GnMCN answer matches with at least one said IGSR of said query GnMCN, and
   c. retrieving in said digital computer system said reference data associated with each said file GnMCN answer.

2. The method as defined in claim 1 in which said query IGSRs and file IGSRs match by overlap.

3. The method as defined in claim 1 in which said query IGSRs and file IGSRs match by embedment.

4. The method as defined in claim 1 further comprising comparing each ISSR of a SpMCN associated with said query GnMCN with each ISSR of said SpMCN associated with each said file GnMCN answer to give a set of file SpMCN answers in which at least one ISSR of each said file SpMCN answer matches with at least one said query ISSR and retrieving said reference data associated with each said file SpMCN answer.

5. The method as defined in claim 4 wherein only said reference data associated with each said file SpMCN answer is retrieved.

6. The method as defined in claim 4 in which said query ISSRs and file ISSRs match by overlap.

7. The method as defined in claim 4 in which said query ISSRs and file ISSRs match by embedment.

8. The method as defined in claim 4 wherein a hierarchical set of generic groups is used to transform said SpMCN representations to said corresponding GnMCN representations.

9. The method as defined in claim 8 wherein said hierarchical set of generic groups is used to represent generic features of said query and file Markush formulations in said query and file SpMCN and associated GnMCN representations.

10. The method as defined in claim 9 wherein said hierarchical set of generic groups comprises any group (G) representative of a chemical entity and wherein said group (G) is further classified as a cyclic group (Cy) and as an acyclic group (Ay) and wherein said cyclic group (Cy) is further classified as a carbocyclic group (Cb) and as a heterocyclic group (Hc); wherein said acyclic group (Ay) is further classified as a carbon group (Ch) and as a noncarbon group (Fg) and wherein said noncarbon group (Fg) is further classified as a terminal group (Ft) and as a connecting group (Fc); and wherein said carbon group (Ch) is further classified as a group (Cg) attached to at least one said terminal group by a multiple bond and as any remaining carbon group (Ak).

11. The method as defined in claim 10 wherein said terminal group (Ft) comprises a single atom other than carbon or hydrogen and any hydrogen atoms attached to said single atom, and said terminal group (Ft) is connected to one or fewer other groups in said hierarchical set of groups; and said connecting group (Fc) comprises a single atom other than carbon or hydrogen and any hydrogen atoms attached to said single atom, and said connecting group (Fc) is connected to two or more groups in said hierarchical set of groups.

12. The method as defined in claim 10 wherein said remaining carbon group (Ak) is further classified as a group comprising six or fewer carbon atoms and as a group comprising more than six carbon atoms.

13. The method as defined in claim 10 wherein said remaining carbon group (Ak) is further classified as a group comprising at least one multiple carbon-carbon bond and as a group comprising any other remaining carbon structure.

14. The method as defined in claim 9 wherein structurely complex SpMCN and GnMCN representations are simplified by shifting a node of variability to another node.

15. The method as defined in claim 8 wherein structurely complex SpMCN and GnMCN representations are simplified by using a null node.

16. The method as defined in claim 9 wherein basic IGSRs and ISSRs are preserved in said GnMCN and SpMCN representations by means of a variable hydrogen.

17. The method as defined in claim 9 wherein each said generic group of each file GnMCN representation is expanded to include all generic groups above and below it in said hierarchy.

18. The method as defined in claim 9 wherein each said group of said hierarchical set of groups used to represent said generic features of said query and said file Markush formulations and to transform said query and file SpMCN representations to GnMCN representations is associated with a set of attributes.

19. The method as defined in claim 18 wherein said set of attributes comprises an identification of noncarbon atoms in said generic group, an identification of an atom count in said generic group, an indication of bond type and number of bonds of said type in said generic group, and an indication of points of attachment of other groups to said generic group.

20. The method as defined in claim 18 wherein said attributes of each query and file group are compared immediately following said matching of each query and file group in said query and file IGSR comparison step to give a set of file GnMCN answers in which all said attributes of all said groups of at least one said IGSR of said query GnMCN are included in all attributes of all corresponding groups of at least one said IGSR of each said file GnMCN.

21. The method as defined in claim 18 wherein said attributes of each said group of each said matching query and file IGSRs are compared after said query and file IGSR comparison step to give a set of file GnMCN answers in which all said attributes of all said groups of at least one said IGSR of said query GnMCN are included in all attributes of all corresponding groups of at least one said IGSR of each said file GnMCN.

22. The method as defined in claim 4 wherein limiting logic in said query and file Markush formulations is stored with said query and file SpMCN representations and is validated after ISSR matching to eliminate any said file SpMCN answer for which said limiting logic no longer allows at least one said ISSR of said query SpMCN to match with at least one ISSR of said file SpMCN answer.

23. The method as defined in claim 9 wherein said query and file ISSRs and IGSRS are tracked by using an indexing system in which a level of variability is assigned to each atom or generic group in said SpMCN and to corresponding generic groups in said associated GnMCN and a variable-group identifier is assigned to each substituent node in said SpMCN and associated GnMCN representations.

24. The method as defined in claim 23 wherein said indexing system is used to store complex SpMCNs and GnMCNs as linked partial representations.

25. The method as defined in claim 17 wherein real-atom segments of a query or file ISSR are rolled-back to a corresponding generic group of said associated IGSR during ISSR matching to allow for generic-group matching when either a corresponding query or file ISSR segment is a generic feature of said Markush formulation.

26. The method as defined in claim 1 further comprising:
a. storing each said file GnMCN representation as an associated generic-group bit string comprising all generic-group screens of all IGSRs of each said file GnMCN representation,
b. comparing a generic-group logic expression comprising all generic-group screens of each IGSR of a query GnMCN with said file generic-group bit strings to give a set of file generic-group bit string answers in which said generic-group logic expression of at least one IGSR of said query GnMCN is included within each file generic-group bit-string answer, and
c. using said GnMCN representations associated with said file specific-atom bit-string answers in said query and file IGSR comparison step.

27. The method as defined in claim 4 further comprising:
a. storing each said file GnMCN representation as an associated generic-group bit string comprising all generic-group screens of all IGSRs of each said file GnMCN representation and as an associated specific-atom bit string comprising all real-atom screens of all ISSRs of each said associated file SpMCN representation,
b. comparing a generic-group logic expression comprising all generic-group screens of each IGSR of a query GnMCN with said file generic-group bit strings to give a set of file generic-group bit string answers in which said generic-group logic expression of at least one IGSR of said query GnMCN is included within each file generic-group bit-string answer, and c. comparing a specific-atom logic expression comprising all specific-atom screens of each ISSR of an SpMCN associated with said query GnMCN with said specific-atom bit strings associated with said generic-group bit-string answers to give a set of file specific-atom bit-string answers in which said specific-atom expression of at least one ISSR of said query SpMCN is included within each said file specific-atom bit-string answer and d. using said GnMCN representations associated with said file specific-atom bit-string answers in said query and file IGSR comparison step.

28. The method as defined in claim 17 further comprising:

a. storing each said file Markush formulation as a single generic-group, specific-atom, and diagnostic-group bit string comprising all generic-group and diagnostic group screens of all IGSRs of each file GnMCN representation and all specific-atom screens of all ISSRs of said associated SpMCN representation, b. forming a query logic expression for each ISSR and corresponding IGSR of a query SpMCN and associated GnMCN comprising sets of generic-group screens and sets of specific-atom screens with corresponding alternative diagnostic-group or diagnostic-group combination screens in which each set of specific-atoms screens is limited to atoms included within boundaries defined by said corresponding diagnostic group or diagnostic-group combination, c. comparing said query logic expression with said file bit strings to give a set of file bit string answers in which said query logic expression of at least one ISSR and associated IGSR of said query SpMCN and associated GnMCN is included within each file bit string answer, and d. using said GnMCN representations associated with said file bit string answers in said query and file IGSR comparison step.

29. The method as defined in claim 17 further comprising:

a. storing a Markush formulation identifier with a screen file index term for each generic-group, diagnostic-group, and specific-atom screen included in all ISSRs and IGSRs of a file SpMCN and associated GnMCN representation, b. forming a query logic expression for each ISSR and corresponding IGSR of a query SpMCN and associated GnMCN comprising sets of generic-group screens and sets of specific-atom screens with corresponding alternative diagnostic-group or diagnostic-group combination screens in which each set of specific-atoms screens is limited to atoms included within boundaries defined by said corresponding diagnostic group or diagnostic-group combination, c. comparing said query logic expressions with said screen identifiers associated with said screen file index terms to give a set of said identifiers in which all required screens of said query logic expression are included within said screen file index terms for a particular identifier, and d. using said GnMCN representations associated with said Markush formulation identifier in said query and file IGSR comparison step.

30. A method for storing and searching Markush formulations using a programmable digital computer system and comprising:

a. forming in said digital computer system a file from a plurality of Markush formulations wherein each said Markush formulation is stored:

(1) as a specific multiple connectivity node (SpMCN) representation of all implicit individual specific structural representations (ISSRs) of each said Markush formulation that includes a hierarchial generic-group representation of all generic features of said Markush formulation, (2) as an associated generic multiple connectivity node (GnMCN) representation of all implicit individual generic structural representations (IGSRs) obtained by a hierarchial generic-group transformation of said SpMCN representation, (3) as a set of attributes associated with each generic group of said GnMCN representation, (4) as a generic-group, specific-atom, and diagnostic-group bit string comprising all generic-group and diagnostic-group screens of all IGSRs of each GnMCN representation and all specific-atom screens of all ISSRs of said associated SpMCN representation, (5) with associated limiting logic from said Markush Formulation, and (6) with associated reference data, b. forming in said digital computer system a query logic expression for each ISSR and corresponding IGSR of a query SpMCN and associated GnMCN comprising sets of generic-group screens and sets of specific-atom screens with corresponding alternative diagnostic-group or diagnostic-group combination screens in which each set of specific-atoms screens is limited to atoms included within boundaries defined by said corresponding diagnostic group or diagnostic-group combination, c. comparing in said digital computer system said query logic expression with file bit strings to give a set of file bit string answers in which said query logic expression of at least one ISSR and associated IGSR of said query SpMCN and associated GnMCN is included within each file bit string answer, d. comparing in said digital computer system each IGSR of said query GnMCN representation with each said IGSR of said file GnMCNs associated with each file bit string answer to give a set of file GnMCN answers in which at least one said IGSR of each said file GnMCN answer matches with at least one said IGSR of said query GnMCN, e. comparing in said digital computer system said attributes of each said group of each said matching query and file IGSR to give a set of file GnMCN answers in which all said attributes of all said groups of at least one said IGSR of said query GnMCN are included in all attributes of all corresponding groups of at least one said IGSR of each said file GnMCN, f. comparing in said digital computer system each ISSR of a SpMCN associated with said query GnMCN with each ISSR of each SpMCN associated with each said file GnMCN answer to give a set of file SpMCN answers in which at least one ISSR of each said file SpMCN answer matches with at least one said query ISSR, g. validating in said digital computer system said limiting logic to eliminate any said file SpMCN answer for which said limiting logic no longer allows at least one said ISSR of said query SpMCN to match with at least one ISSR of said file SpMCN answer, and h. retrieving in said digital computer system said reference data associated with each said file SpMCN answer.

31. The method as defined in claim 30 further comprising means for graphic structure input, means for establishing and maintaining a telecommunications interface, means for query and search control, means for database management, means for screen search, means for group-by-group, attribute, and atom-by-atom comparison, means for logic condition verification, means for answer retrieval and online answer output, means for off-line answer printing, and means for said system support, maintenance, and backup.

* * * * *